United States Patent
Ding et al.

(10) Patent No.: US 11,623,107 B2
(45) Date of Patent: Apr. 11, 2023

(54) PARTICLE ARC THERAPY

(71) Applicant: William Beaumont Hospital, Royal Oak, MI (US)

(72) Inventors: Xuanfeng Ding, Bloomfield Hills, MI (US); Xiaoqiang Li, Troy, MI (US); Di Yan, Auburn Hills, MI (US)

(73) Assignee: WILLIAM BEAUMONT HOSPITAL, Royal Oak, MI (US)

( * ) Notice: Subject to any disclaimer, the term of this patent is extended or adjusted under 35 U.S.C. 154(b) by 63 days.

(21) Appl. No.: 17/314,395

(22) Filed: May 7, 2021

(65) Prior Publication Data

US 2021/0260406 A1 Aug. 26, 2021

Related U.S. Application Data

(63) Continuation-in-part of application No. 16/083,354, filed as application No. PCT/US2017/021837 on Mar. 10, 2017, now Pat. No. 11,027,151.

(Continued)

(51) Int. Cl.
*A61N 5/10* (2006.01)
*G16H 40/63* (2018.01)
*G16H 20/40* (2018.01)

(52) U.S. Cl.
CPC ......... *A61N 5/1031* (2013.01); *A61N 5/1065* (2013.01); *A61N 5/1071* (2013.01);
(Continued)

(58) Field of Classification Search
CPC .. A61N 5/1031; A61N 5/1081; A61N 5/1047; A61N 5/1065; A61N 5/1071; A61N 2005/1087; G16H 20/40; G16H 40/63
(Continued)

(56) References Cited

U.S. PATENT DOCUMENTS 3,980,885 A 9/1976 Steward et al.
5,825,845 A 10/1998 Blair et al.
(Continued)

FOREIGN PATENT DOCUMENTS

CN 101983085 A 3/2011
CN 102596316 A 7/2012
(Continued)

OTHER PUBLICATIONS

Berman, Abigail T., et al. Proton Beam Therapy for Non-Small Cell Lung Cancer: Current Clinical Evidence and Future Directions. Cancers 2015, 7, 1178-1190.
(Continued)

*Primary Examiner* — Kiet T Nguyen
(74) *Attorney, Agent, or Firm* — Honigman LLP; Thomas J. Appledorn; Jonathan P. O'Brien

(57) ABSTRACT

A method of optimizing delivery of a particle beam at a target is disclosed. The particle beam is delivered from an output device at a plurality of control points. In implementations, the method comprises delivering a substantially continuous particle beam about the plurality of control points, iteratively adjusting a delivery time of the substantially continuous particle beam about the plurality of control points, and processing to undertake at least one of (i) pre-defining energy layers based on one or both of the control points and a control point sampling frequency, or (ii) sorting the energy layers.

20 Claims, 16 Drawing Sheets

Related U.S. Application Data

(60) Provisional application No. 62/410,674, filed on Oct. 20, 2016.

(52) U.S. Cl.
CPC ........... *A61N 5/1081* (2013.01); *G16H 20/40* (2018.01); *G16H 40/63* (2018.01); *A61N 2005/1087* (2013.01)

(58) Field of Classification Search
USPC ..................................................... 250/492.3
See application file for complete search history.

(56) References Cited

U.S. PATENT DOCUMENTS

| | | | |
|---|---|---|---|
| 8,000,435 | B2 | 8/2011 | Bertram et al. |
| 8,053,736 | B2 | 11/2011 | Ahnesjo et al. |
| 8,897,857 | B2 | 11/2014 | Tome et al. |
| 8,963,108 | B2 | 2/2015 | Matteo et al. |
| 9,012,866 | B2 | 4/2015 | Benna et al. |
| 9,207,193 | B2 | 12/2015 | Censor et al. |
| 9,301,384 | B2 | 3/2016 | Zwart et al. |
| 9,302,122 | B2 | 4/2016 | Balakin |
| 9,415,241 | B2 | 8/2016 | Ito et al. |
| 9,817,150 | B2 | 11/2017 | Sossong |
| 2005/0037484 | A1 | 2/2005 | Staimer et al. |
| 2005/0161051 | A1 | 7/2005 | Pankratov et al. |
| 2005/0197564 | A1 | 9/2005 | Dempsey |
| 2010/0020931 | A1 | 1/2010 | Otto et al. |
| 2010/0051824 | A1 | 3/2010 | Nord et al. |
| 2010/0108903 | A1 | 5/2010 | Bert et al. |
| 2010/0127184 | A1 | 5/2010 | Balakin |
| 2010/0327188 | A1 | 12/2010 | Bert et al. |
| 2013/0142310 | A1 | 6/2013 | Fahimian et al. |
| 2014/0121442 | A1 | 5/2014 | Matteo et al. |
| 2015/0087885 | A1 | 3/2015 | Boisseau et al. |
| 2015/0217135 | A1 | 8/2015 | Bohsung et al. |
| 2015/0314140 | A1 | 11/2015 | Verhaegen et al. |
| 2016/0016008 | A1 | 1/2016 | Kelly |
| 2016/0067525 | A1 | 3/2016 | Bouchet et al. |
| 2018/0020535 | A1* | 1/2018 | Cooley ................ A61B 5/0036 |
| 2018/0280729 | A1* | 10/2018 | Poulsen ................ A61N 5/1075 |

FOREIGN PATENT DOCUMENTS

| | | |
|---|---|---|
| CN | 104941076 A | 9/2015 |
| CN | 107497059 A | 12/2017 |
| EP | 2750484 A1 | 2/2014 |
| EP | 2853292 A1 | 1/2015 |
| EP | 2851104 A1 | 3/2015 |
| FR | 2839894 A1 | 11/2003 |
| JP | 2015-97683 A | 5/2015 |
| JP | 2015-532509 A | 11/2015 |
| TW | 201345581 A | 11/2013 |
| WO | 2011084878 A1 | 7/2011 |
| WO | 2016014422 A1 | 1/2016 |
| WO | WO-2017156419 A1 | 9/2017 |

OTHER PUBLICATIONS

Cao, Wenhua, et al., "Proton Energy Optimization and Reduction for Intensity-Modulated Proton Therapy" Physics in Medicine & Biology, vol. 59, No. 21 2014.

Carabe-Fernandez, Alejandro Symposium presented to American Association of Physicists in Medicine in Austin, TX on Jul. 22, 2014 entitled "Development and delivery of biologically optimized treatment plans in proton radiotherapy", 60 pages.

Carabe-Fernandez, A., et al. SU-E-T-640: Proton Modulated Arc Therapy Using Scanned Pencil Beams Medical Physics vol. 42, Issue 6 part 22, Jun. 2015, p. 3483.

Ding, X., et al. Spot-Scanning Proton Arc (SPArc) Therapy: The First Robust and Delivery-Efficient Spot-Scanning Proton Arc Therapy. Int'l Journal of Radiation Oncology Biology Physics, vol. 96(5), 2016, pp. 1107-1116.

Ding, X., et al. WE-F-16A-03: 3D Printer Application in Proton Therapy: A Novel Method to Deliver Passive-Scattering Proton Beams with a Fixed Range and Modulation for SRS and SRT. Medical Physics vol. 41, issue 6, Jun. 2014, p. 514.

Flynn, R.T., et al. Comparison of intensity modulated x-ray therapy and intensity modulated proton therapy for selective subvolume boosting: a phantom study. Physics in Medicine and Biology 52(2) (2007) pp. 6073-6091.

Kraus, Kim Melanie. Dissertation submitted to the Combined Faculties for the Natural Sciences and for Mathematics of the Ruperto-Carola University of Heidelberg, Germany for the degree of Doctor of Natural Sciences. Jan. 15, 2014, 143 pages.

Otto, Karl "Volumetric modulated arc therapy: IMRT in a single gantry arc", Medical Physics, vol. 35, Issue 1, Jan. 2008, pp. 310-317.

Rechner, Laura A., et al. Risk of radiogenic second cancers following volumetric modulated arc therapy and proton arc therapy for prostate cancer. Phys Med Biol. Nov. 7, 2012; 57(21): 7117-7132.

Sandison, G.A. Phantom Assessment of Lung Dose from Proton Arc Therapy. Int. J. Radiation Oncology Biol. Phys., vol. 38, No. 4, pp. 891-897, 1997.

Seco, Joao, et al. Proton Arc Reduces Range Uncertainty Effects and Improves Conformality Compared with Photon Volumetric Modulated Arc Therapy in Stereotactic Body Radiation Therapy for Non-Small Cell Lung Cancer. International Journal of Radiation Oncology, vol. 87, No. 1, pp. 188-194, 2013.

Sengbusch, E., et al. Maximum proton kinetic energy and patient— generated neutron fluence considerations in proton beam arc delivery radiation therapy. Med. Phys. 36 (2), Feb. 2009, pp. 364-372.

Van De Water, S., et al., "Improved Efficiency of Multi-Criteria IMPT Treatment Planning Using Iterative Resampling of Randomly Placed Pencil Beams." Phys Med Biol 2013; 58(19):6969-6983.

Van De Water, S., et al. Shortening Delivery Times of Intensity Modulated Proton Therapy by Reducing Proton Energy Layers During Treatment Plan Optimization. Int'l Journal of Radiation Oncology, vol. 92(2), 2015, pp. 460-467.

Van De Water, Steven. Dissertation published entitled Optimizing Planning and Delivery of High-Precision Robotic Radiotherapy and Intensity-Modulated Proton Therapy. Jun. 9, 2015, p. 152.

Zhang, Miao, et al., "The Energy Margin Strategy for Reducing Dose Variation due to Setup Uncertainty in Intensity Modulated Proton Therapy (IMPT) Delivered with Distal Edge Tracking (DET)" Journal of Applied Clinical Medical Physics, vol. 13, No. 5, 2020, pp. 170-180.

Zou, Wei, et al., "Potential of 3D Printing Technologies for Fabrication of Electron Bolus and Proton Compensators." Journal of Applied Clinical Medical Physics, vol. 16, No. 3, 2015 pp. 90-98. International Search Report and Written Opinion for PCT/US17/21837 dated Jun. 2, 2017.

Mo, X., et al. "TH-C-BRB-07: Treatment Planning with Multiple Spot Sizes to Improve Delivery Efficiency in Intensity Modulated Proton Therapy." Medical Physics 38(6):3854, Jun. 2011 Abstract only.

Chin, L.S., et al. "Treatment Planning for Sterotactic Radiosurgery." Principles and Practice of Stereotactic Radiosurgery. DOI 10.1007/978-1-4614-8363-2-6 Springer Science+Business Media New York 2015, chpt 6, p. 90.

\* cited by examiner

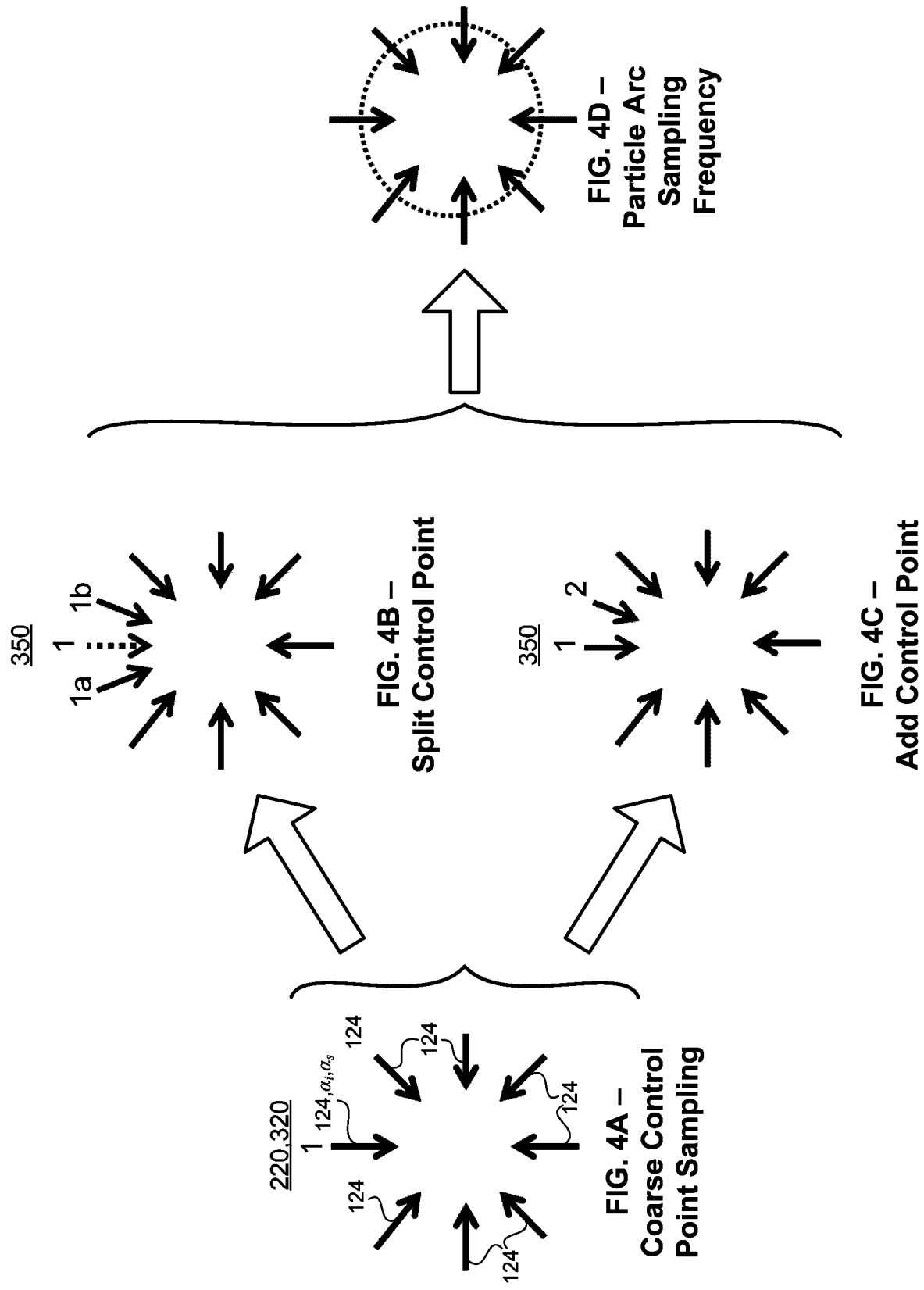

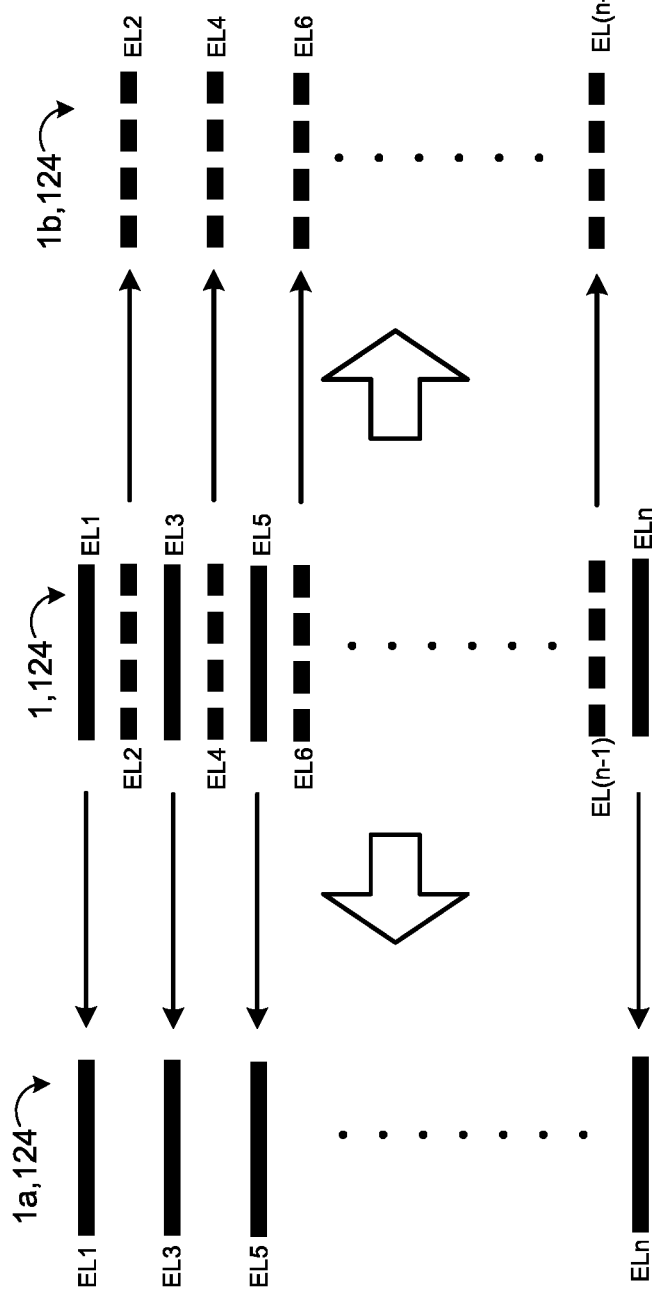

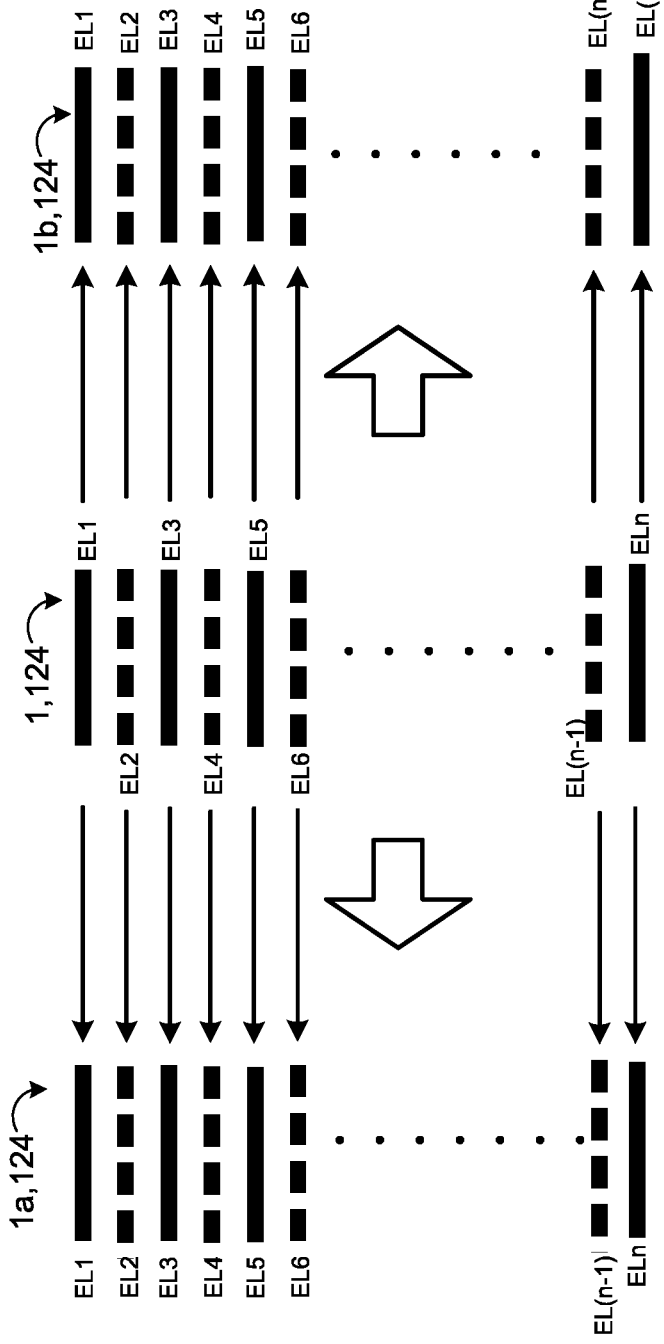

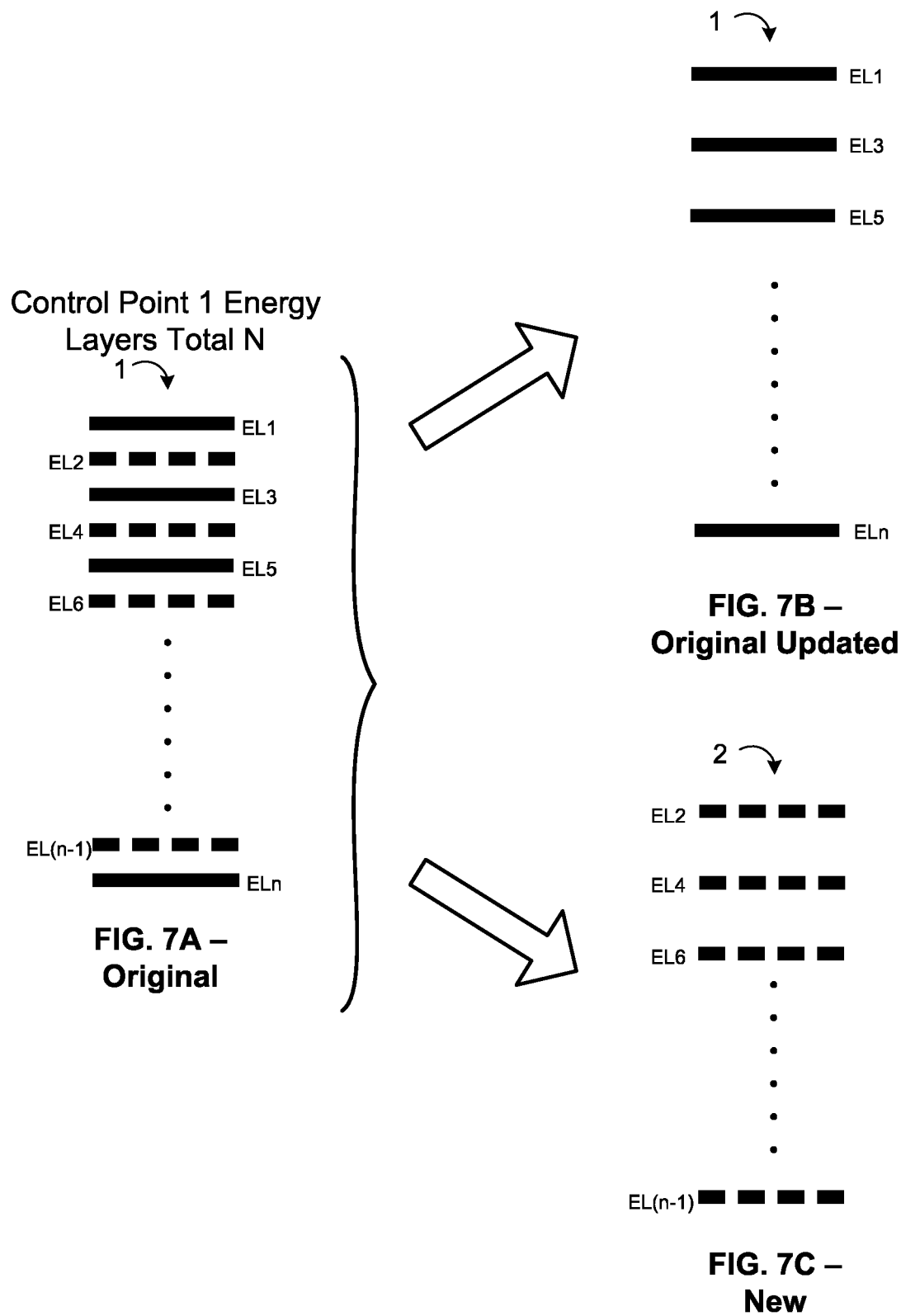
FIG. 7A – Original
FIG. 7B – Original Updated
FIG. 7C – New

PARTICLE ARC THERAPY

CROSS REFERENCE TO RELATED APPLICATIONS

This patent application is a continuation-in-part of U.S. application Ser. No. 16/083,354, filed Sep. 7, 2018, which claims the benefit of PCT International Application No. PCT/US2017/021837, filed Mar. 10, 2017, which claims the benefit under 35 U.S.C. § 119(e) to U.S. Provisional Application 62/410,674, filed on Oct. 20, 2016, U.S. Provisional Application 62/337,097, filed on May 16, 2016, U.S. Provisional Application 62/306,403, filed on Mar. 10, 2016, and U.S. Provisional Application 62/306,413, filed on Mar. 10, 2016. The disclosures of these prior applications are considered part of this disclosure and are hereby incorporated by reference in their entireties.

TECHNICAL FIELD

This disclosure relates to systems and methods for providing substantially continuous charged particle arc therapy.

BACKGROUND

Charged particle therapy employs beams of energized protons, carbon ions, or other charged particles. Currently, one of the most common types of particle therapy is proton therapy. Proton therapy, also referred to as proton beam therapy, is a medical procedure that uses a beam of protons to irradiate diseased tissue. One of the advantages of proton therapy in comparison to the conventional photon radiotherapy such as, X-ray or gamma ray, for example, for the treatment of cancer, is the reduced integral dose to the patient. Integral dose can refer to a total amount of energy experienced by the patient during radiative kinds of treatments. Proton therapy can help to minimize damage to tissues and structures while focusing a preferred dose upon the target tissue.

Proton therapy may provide superior tumor coverage and deliver a lower integral dose to a patient's body compared to conventional radiotherapy. As compared to traditional passive-scattering proton therapy, spot-scanning proton therapy techniques may provide superior target coverage by scanning the target spot-by-spot and layer-by-layer similar to three-dimensional printing techniques. But current spot-scanning proton therapy beam delivery techniques may be limited in performance and may only be capable of delivering limited proton beams in one treatment fraction (i.e., normally one treatment fraction only consists of 1-4 treatment fields).

SUMMARY

One aspect of the disclosure provides a method of optimizing delivery of a particle beam at a target, wherein the particle beam is delivered from an output device at a plurality of control points. The method comprises delivering a substantially continuous particle beam about the plurality of control points, iteratively adjusting a delivery time of the substantially continuous particle beam about the plurality of control points, identifying an initial set of control points, and providing a first group of optimized beams, wherein each optimized beam of the first group of optimized beams is configured to be output at a first control point and steered towards one or more energy layers that are associated with one or more monitor unit (MU), providing a second group of optimized beams, each optimized beam of the second group of optimized beams configured to be output at the first control point and having a reduced number of energy layers, increasing a number of the initial control points, and maintaining a total number of energy layers as one of equal to, more than, or less than a total number of energy layers associated with the initial control points during movement of the beam between the plurality of control points, wherein increasing the number of initial control points comprises adding one or more adjacent control points to each initial control point, the adjacent control point having a fraction number of the total energy layers or MU of the initial control point.

Implementations of the disclosure may include one or more of the following optional features. In some implementations, the delivery time of the substantially continuous particle beam is iteratively adjusted via one or more of filtering the one or more energy layers, merging the one or more energy layers, re-distributing the one or more energy layers, or adding new energy layers to the one or more energy layers.

The delivery time of the substantially continuous particle beam may be iteratively adjusted via one or more of filtering one or more proton spots, merging the one or more proton spots, re-distributing the one or more proton spots, or adding new proton spots within and between the one or more proton spots.

The delivery time of the substantially continuous particle beam may be iteratively adjusted via adjusting one or more of the MU of one or more proton spots within and between the control points or an intensity of the one or more proton spots within and between the control points.

The delivery time of the substantially continuous particle beam may be at least partially determined based on a machine-specific delivery sequence model ($DSM_{arc}$) that is calculated using a plurality of machine specific system parameters and a plurality of user defined parameters. The plurality of machine specific system parameters may include a delivery tolerance window, gantry mechanical limitations, and mechanism of control point connections. The plurality of user defined parameters may include a defined total SPArc delivery time or speed, a delivery tolerance window, and momentum or speed change during delivery of the substantially continuous particle beam.

Another aspect of the disclosure provides a method of optimizing delivery of a particle beam at a target, wherein the particle beam is delivered from an output device at a plurality of control points. The method comprises delivering a substantially continuous particle beam about the plurality of control points, iteratively adjusting a delivery time of the substantially continuous particle beam about the plurality of control points, and processing to undertake at least one of (i) pre-defining energy layers based on one or both of the control points and a control point sampling frequency, or (ii) sorting the energy layers.

This aspect may include one or more of the following optional features. In some implementations, the delivery time of the substantially continuous particle beam is iteratively adjusted via one or more of filtering the one or more energy layers, merging the one or more energy layers, re-distributing the one or more energy layers, or adding new energy layers to the one or more energy layers.

The delivery time of the substantially continuous particle beam may be iteratively adjusted via one or more of filtering one or more proton spots, merging the one or more proton spots, re-distributing the one or more proton spots, or adding new proton spots within and between the one or more proton spots.

The delivery time of the substantially continuous particle beam may be iteratively adjusted via adjusting one or more of the MU of one or more proton spots within and between the control points or an intensity of the one or more proton spots within and between the control points.

The delivery time of the substantially continuous particle beam may be at least partially determined based on a machine-specific delivery sequence model ($DSM_{arc}$) that is calculated using a plurality of machine specific system parameters and a plurality of user defined parameters. The plurality of machine specific system parameters may include a delivery tolerance window, gantry mechanical limitations, and mechanism of control point connections. The plurality of user defined parameters may include a defined total SPArc delivery time or speed, a delivery tolerance window, and momentum or speed change during delivery of the substantially continuous particle beam.

Another aspect of the disclosure provides a system comprising data processing hardware, and memory hardware in communication with the data processing hardware. The memory hardware stores instructions that when executed on the data processing hardware cause the data processing hardware to perform operations comprising delivering a substantially continuous particle beam at a target about a plurality of control points, iteratively adjusting a delivery time of the substantially continuous particle beam about the plurality of control points, identifying an initial set of control points, providing a first group of optimized beams, wherein each optimized beam of the first group of optimized beams is configured to be output at a first control point and steered towards one or more energy layers that are associated with one or more monitor unit (MU), providing a second group of optimized beams, each optimized beam of the second group of optimized beams configured to be output at the first control point and having a reduced number of energy layers, increasing a number of the initial control points, and maintaining a total number of energy layers as one of equal to, more than, or less than a total number of energy layers associated with the initial control points during movement of the beam between the plurality of control points, wherein increasing the number of initial control points comprises adding one or more adjacent control points to each initial control point, the adjacent control point having a fraction number of the total energy layers or MU of the initial control point.

This aspect may include one or more of the following optional features. In some implementations, the delivery time of the substantially continuous particle beam is iteratively adjusted via one or more of filtering the one or more energy layers, merging the one or more energy layers, re-distributing the one or more energy layers, or adding new energy layers to the one or more energy layers.

The delivery time of the substantially continuous particle beam may be iteratively adjusted via one or more of filtering one or more proton spots, merging the one or more proton spots, re-distributing the one or more proton spots, or adding new proton spots within and between the one or more proton spots.

The delivery time of the substantially continuous particle beam may be iteratively adjusted via adjusting one or more of the MU of one or more proton spots within and between the control points or an intensity of the one or more proton spots within and between the control points.

The delivery time of the substantially continuous particle beam may be at least partially determined based on a machine-specific delivery sequence model ($DSM_{arc}$) that is calculated using a plurality of machine specific system parameters and a plurality of user defined parameters. The plurality of machine specific system parameters may include a delivery tolerance window, gantry mechanical limitations, and mechanism of control point connections.

The details of one or more implementations of the disclosure are set forth in the accompanying drawings and the description below. Other aspects, features, and advantages will be apparent from the description and drawings, and from the claims.

DESCRIPTION OF DRAWINGS

FIGS. 4A-4D are schematic views of example control point resampling techniques.

FIGS. 5A-5C are schematic views of example energy layer reorganization and re-distribution techniques.

FIGS. 6A-6C are schematic views of example energy layer reorganization and re-distribution techniques.

FIGS. 7A-7C are schematic views of example energy layer reorganization and re-distribution techniques.

Like reference symbols in the various drawings indicate like elements.

DETAILED DESCRIPTION

This description describes implementations and methods of particle spot-scanning therapy to deliver a particle beam in a substantially continuous manner. In implementations, a particle beam is delivered in a substantially continuous manner in connection with one or both of a gantry, a couch, or other arrangements whereby an impact angle of the particle beam is altered. Throughout the description hereof, the term proton is used as an example of a particle. It is to be appreciated that the invention hereof should not be so limited to a proton and the inventors recognize that the principles are applicable to all particles and the terms are generally interchangeable in the context of this disclosure.

The inventors hereof have identified inefficiencies associated with conventional spot-scanning proton therapy (e.g., Intensity Modulated Proton Therapy (IMTP) and the like). Namely, conventional techniques may not maximize an effectively continuous proton delivery. For example, and perhaps among other things, such conventional systems may effectively cease proton delivery when changing between impact angles (defined below) with reference to a desired target (defined below) (a proton machine will typically first adjust the impact angle and then deliver the proton beam and thereby limit treatment efficiency). In addition, stopping and starting of the proton delivery can impact the calibration of the proton delivery system as some systems experience a vibration when switching between delivery and non-delivery.

Figure 1:
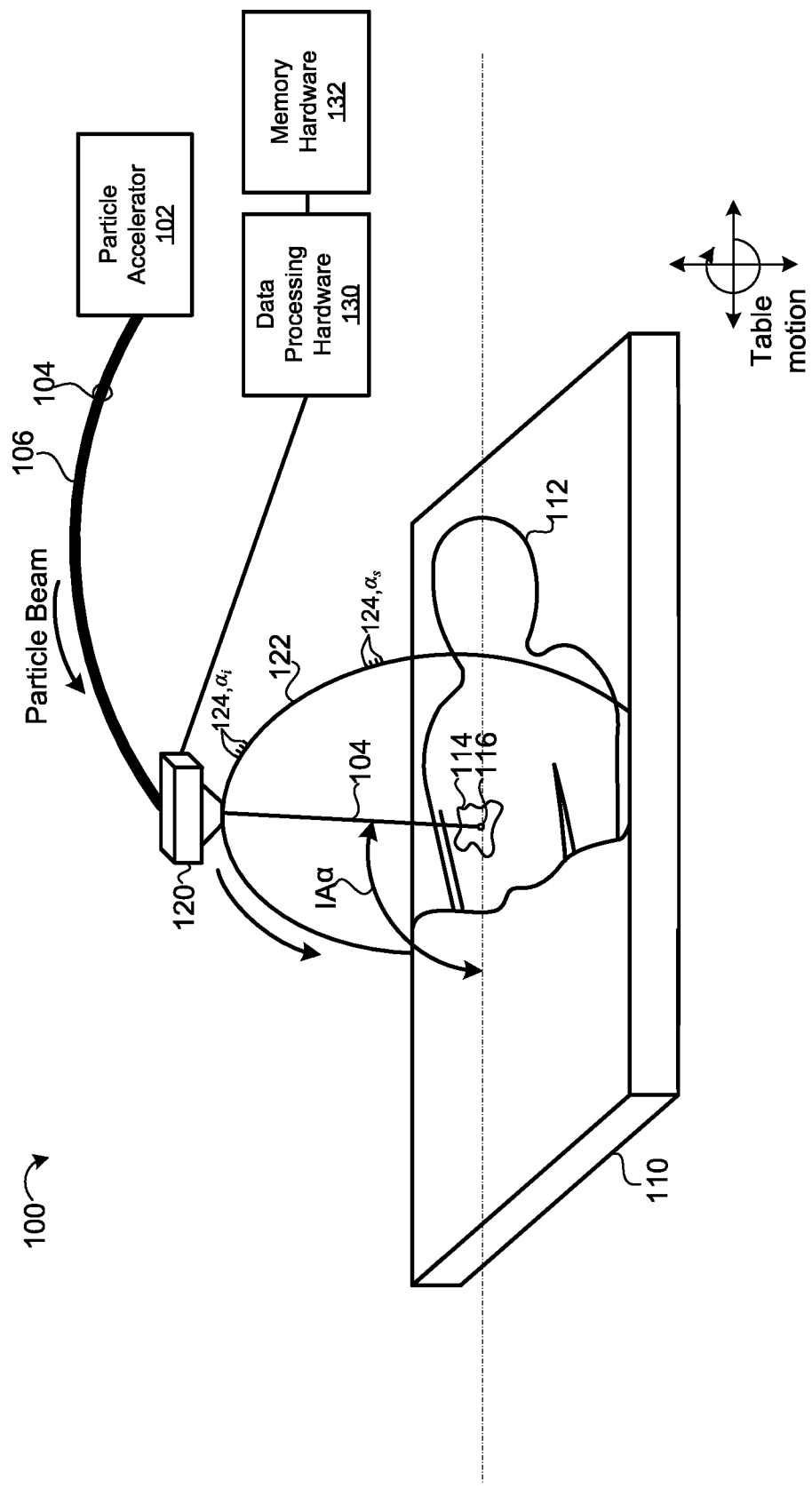
FIG. 1 is a schematic view of an exemplary system according to implementations.

With reference now to the Figures, FIG. 1 illustrates an implementation of a proton delivery system 100 for delivering a substantially continuous proton treatment to a patient using one or more arc trajectories or non-iso centric movement with couch and gantry at same time. As illustrated, system 100 includes a particle accelerator 102 that delivers one or more proton beams 104, via a beam line 106, to output 120. Particle accelerator 102 accelerates charged particles and arranges charged particles in well-defined beams before extracting proton beams 104 via beam line 106. Examples of particle accelerators include colliders, cyclotrons, synchrotrons, laser proton accelerators, and the like.

In some implementations, accelerator 102 may be positioned remote from output 120 such that accelerator 102 may be centrally located and selectively connectable to multiple outputs 120.

With continued reference to FIG. 1, beam 104 is output 120 towards a desired target of a body 114 having an isocenter or multiple continuous moving isocenters 116 located on a treatment station 110. Beam is directed at the desired target with respect to an impact angle (IA) relative to the current isocenter 116, which will be described in additional detail below. For ease of disclosure, body 114 may be referenced herein as a tumor, and treatment station 110 will be referenced as a couch or a table, yet it is to be appreciated that other targets and treatment stations are contemplated and the disclosure should not be limited to the examples.

Impact angle as used in this disclosure is the angle in which body 114 experiences beam 104 and is shown as the angle between a plane that extends through the isocenter 116 of body 114 (parallel with treatment station 110) and beam 104. For ease of disclosure, each change in impact angle IA is the result of movement of one or both of (i) adjustment of output 120 about a gantry 122 among a plurality of control points 124 (as shown in the Figures) with respect to body 114, (ii) adjustment of body 114 at a plurality of control points 124 with respect to output 120, via movement of the treatment station 110 or the like, (iii) movement of output 120 and movement of body 114, each with respect to one another independently or simultaneously, or (iv) other suitable means.

In an implementation, magnets (not shown) may be provided in or about output 120 and/or along the beam line 104 that have adjustable currents to selectively adjust beam 104. In an implementation, a degrader or energy selection system (such as a wedge or the like) in the beamline may be provided to offer a selectively adjustable proton energy; for example, different energies may be more desirable based on an appropriate treatment. A range shifter (sometimes referred to as a bolus) (not shown) may be used (e.g., in the gantry nozzle) to attenuate the proton energy. A proton multi-leaf collimation system may be used to sharp the proton spot lateral penumbra during the delivery and rotation of the gantry, couch, or the like. Such an attenuation and selection may be utilized to alter the energy of the proton beam and achieve desired depths of treatment. For purpose of this disclosure, different depths within body 114 will be referenced as energy layers. Multiple energy layers can be used in the system 110 described herein to effectively treat a three-dimensional tumor 114.

In some examples, range shifter may be used to degrade, or broaden, beam 104. During a session, range shifter may move continuously during the gantry rotation with respect to isocenter 116. Range shifter may be used to optimize an air gap between the range shifter and the patient's skin to ensure the proton beam 104 reaches a designated position 116 that has a pre-defined size and is generally associated with tumor 114.

In some arrangements, system 100 may be deployed in conjunction with a configuration system, such as, for example, an imaging system. In implementations, the configuration system may be a Cone-Beam Computed Tomography (CBCT), a Fluoroscope, stereotactic imaging system, surface matching camera system, or other similar devices that can monitor the patient during the proton beam delivery.

In an implementation, system 100 delivers a substantially continuous beam of protons 104 during a session and throughout any changes to one or both of the impact angle (IA)—whether such impact angle is altered via changing control points via (i) movement of output 120 along a gantry G, (ii) movement of couch; or (iii) a combination thereof. For ease of disclosure, the remainder of this disclosure will disclose embodiments where impact angle is altered by movement of output 120 about control points 124 along a gantry G but it is equally contemplated that IA may be otherwise altered and the scope of this disclosure should not be limited to the disclosed embodiments.

As described in more detail below, system 100 may be generally configured to minimize a number of energy layers for one, some, or all of the beams that may be directed toward one or more control points. To achieve such minimization, in an implementation, system 100 may undertake one or more of the following steps (i) filters lower weighted energy layers from the session, (ii) filters lower weighted proton spots, and (iii) re-arranges the remaining energy layers and/or proton spots between two or more consecutive control points which thereby maintains the same robust plan quality and is formatted to yield a substantially continuous step-and-shoot proton arc delivery.

A session will now be described. In an implementation, output 120 emits beam 104 towards a desired location of tumor 114 of patient 112 at a number of impact angles IA; accordingly, control points 124. As an example, output 120 moves about a track 122 in a manner that facilitates the proton beam 104 to reach target 114 about different impact angles IA and at a number of associated control points 124. For example, system 100 may be configured to provide an optimized session in accordance with a cancer treatment session.

In implementations, system 100 provides session algorithms and platforms (i.e., executing on the data processing hardware 130) to deliver an optimized session to patient 112 via output 120. In an implementation, system 100 maximizes one or more sessions through: (a) determining an optimized number of energy layers per control point (e.g., 1-6 energy layers), (b) determining an optimum number of control points (and/or impact angles IA), and (c) performing spot beam weighting and positioning at each control point 124 (and/or imaging angle). In other words, system 100 provides a session that optimizes the number, and position, of control points 124 (and/or impact angles) and identifies the weight and position of each beam reaching a desired location about tumor 114.

In an implementation, system 100 may include one or more substantially continuous scanning modes, such as, but not limited to a step-and-shoot spot scanning mode, a continuous arc delivery mode, or other delivery modes. In a step-and-shoot spot scanning mode, system 100 switches energy layers of beam 104 by selecting different energy layers (e.g., by using degrader and adjusting magnets as described above) to direct beam 104 to the desired positions about target 114 among various impact angles (IA) and while the imaging angle (IA) is adjusting (e.g., while gantry is rotating between control points 124).

In implementations, system 100 delivers one or more beams 104 at each control point 124 (and/or impact angle (IA)) and, in some embodiments, each proton beam 104 may be associated with an energy layer. In an implementation, each energy layer may be different and, in other implementations some or all of the energy layers may be common.

In some implementations, a step-and-shoot approach may save time by switching among one or more energy layers while adjusting impact angles IA. In other words, system 100 can change the one or more beams 104 between one or more energy layers during the IA adjustment, thereby resulting in a reduced overall session time. For example, considering a gantry rotation speed of three degrees per second, during the one second it may take gantry to rotate to a next control point three degrees away, system 100 may change the one or more energy layers in which beam 104 is directed.

As earlier described, in some examples, at each control point, beam 104 may include 1-6 energy layers. In an exemplary session, each control point 124 may include a beam 104 having one energy layer. In alternative sessions, it may be desired to reach one or more energy layers for one or more control points 124—in which case, system 100 changes energy layers without gantry rotation at such control points 124. As a result, system 100 may provide multiple beams 104, each having a different energy layers. Both scenarios result in full or partial tumor 114 (three-dimensional) coverage from multiple impact angles IA and/or control points 124 thereby providing a system that delivers a full and robust tumor coverage dose through one or more arc trajectories.

In a continuous arc delivery mode, instead of delivering the proton beam 104 at each static control point 124, system 100 continuously delivers the proton beam 104 while changing the impact angle IA or control points 124. So instead of utilizing discrete control points 124 or impact angles IA that are described above for the step and shoot examples, in a continuous arc delivery mode, system 100 considers each control point 124 or impact angle IA as being within an angular range (e.g., $-0.5<\alpha<0.5$ degrees) or a position range (e.g., $-1$ mm$<$x$<+1$ mm couch position) which will be referred to herein as a control point sampling frequency (CPSF). It will be appreciated, therefore, that a higher control point sampling frequency indicates a smaller angle or position spread between adjacent control points. As a result, such discrete radiation delivery through step & shoot mode through different control points will be a close approximation to the continuous radiation delivery with such control point range (e.g., from $-10$ degree to 20 degree partial arc and/or $-10$ cm to $+20$ cm couch movements).

In implementations, and as described in the examples that follow, control point sampling frequency (CPSF) may be introduced to effectively minimize the dosimetric difference witnessed upon body 114 as compared with the previously described step-and-shoot delivery. For example, the desired control point sampling frequency of the continuous session may suggest that four degrees between each effective control point (e.g., from 0 to 4 degrees) is substantially dosimetrically equal to a step and shoot session delivered at 2 degrees.

In an implementation, there is almost no dosimetric difference between statically delivering the proton beam 104 at one degree (step-and-shoot mode) and dynamically delivering the proton beam from 0.5 to 1.5 degree (continuous arc delivery mode). But in the latter continuous case, delivering proton beam 104 continuously during the gantry rotation having a CPSF of 1 degree—additional time may be saved and gantry inertia, vibrations during stop and start or other mechanical issues can be avoided.

In some implementations, system 100 may be configured to determine an optimized number of control points 124 and re-sampling the control points 124 to achieve a desired control point sampling frequency CPSF. In addition, system 100 may be configured to filter energy layers associated with each control point 124 such that the energy layers are weighted and those having low monitor units (MU) are removed. In some implementations, system 100 may also be configured to organize and allocated energy layers to nearby control points 124 instead of, prior to, or after filtering the energy layers.

To improve the calculation and optimization speed, system 100 may employ a progressive dose grid sampling method, which may be defined by the unit of energy deposition in the Computer Tomography (CT) set or patient body. For example, one (1) cubic center size cube consists of 1000 dose grids with 1 mm×1 mm×1 mm size or 1 dose grid with 10 mm×10 mm×10 mm size. An implementation of such a progressive dose grid sampling method may utilize a coarse dose grid size, and then progressively reduce the dose grid size during the optimization.

System 100 includes memory hardware 132 in communication with the data processing hardware 130. The memory hardware 132 stores instructions that when executed on the data processing hardware 130 cause the data processing hardware 132 to perform operations, such as the method described with respect to FIG. 2, the method described with respect to FIGS. 3A-3C, or the method described with respect to FIG. 3D.

FIG. 2 describes an example arrangement of operations for a method 200 of operating system 100. At block 210, system 100 pre-defines a proton arc range (i.e., an initial angle $\alpha_i$ and a stop angle $\alpha_s$) associated with gantry opening 122 and/or the rotation of table 110 or couch/table translation movement (i.e., an initial position $x_1$ and a stop position $x_s$). In some examples, a user defines the proton arc range. For example, system 100 sets an initial angle $\alpha_i$ or position of control point 124 (i.e., gantry location) of proton output 120 emitting beam 104. In some examples, system 100 sets the initial angle $\alpha_i$ at 10 degrees and an initial stop angle $\alpha_s$ at 60 degrees. In some examples, if the gantry is capable of rotating at 360 degrees, then the initial angle $\alpha_i$ is set at zero degrees and the initial stop angle $\alpha_s$ is set at 360 degrees. Other values of the initial angles $\alpha_i$ and stop angles $\alpha_s$ are possible as well. In some implementations, since table/couch 110 is capable of translational movement, system 100 also sets a table/couch initial angle and position for the table/couch 110 with respect to proton output 120. In this case, control point 124 is defined as table translation and rotational movement, for example every one centimeter, every two centimeters, or other every one degree, every two degree as well. Therefore, in some implementations, system 100 defines an initial angle $\alpha_i$ for output 120 and/or an initial angle for the table/couch 110 resulting in the rotation of one or both of the proton output 120 and the table/couch 110. As a result, system 100 considers the rotation of one or both of the output 120 and the table/couch 110 with respect to one another to generate the proton arc range.

At block 220, system 100 determines a coarse control point sampling frequency CPSF as shown in FIG. 4A. In other words, system 100 identifies a number of gantry locations or control points 124. As shown in FIG. 4A, system 100 identifies eight control points 124 within the gantry's 360-degrees of freedom. Other number of coarse control points may be used as well.

Referring back to FIG. 2, at block 230 system 100 determines an optimization treatment plan for patient 112. The optimization treatment plan determines a beam dose plan used by the beam 104 to irradiate body 114 as well as spare nearby tissue. In some examples, system 100 considers the anatomy of patient 112, and determines a beam energy (i.e., energy layer), a beam spot position, and a number of protons to be delivered in each beam 104 to patient 112. In addition, system 100 optimizes a dose distribution in patient 112 (for example, robustness optimization by considering daily treatment setup and proton range uncertainties; radiobiology effect (RBE) optimization by considering radiation biology effect of the proton beam), which allows a robust dose distribution or biological effective dose to body 114 as well as spare the healthy tissue and organs under these uncertainties. In some implementations, system 100 determines the effects of potential changes to body 114, for example, and adjusts the treatment plan accordingly, which may be referred to as treatment plan adaptation. Some changes may include, the patient gaining or losing weight, the tumor changing size, or other considerations. By using robust optimization, system 100 is capable of providing optimal robust target coverage while sparing healthy tissue.

At block 240, system 100 may first (A) optionally optimize the sampling frequency of the control points 124 (e.g., iteratively increasing control points numbers at block 240), the energy layer(s) and proton spots associated with each control point 124 to optimize the delivery efficiency for delivering proton beam 104, resulting in an optimized treatment plan. In other words, system 100 uses a random iterative process that selects the optimized energy layers and spot position and weightings of beam 104 for the treatment.

Figure 2A:
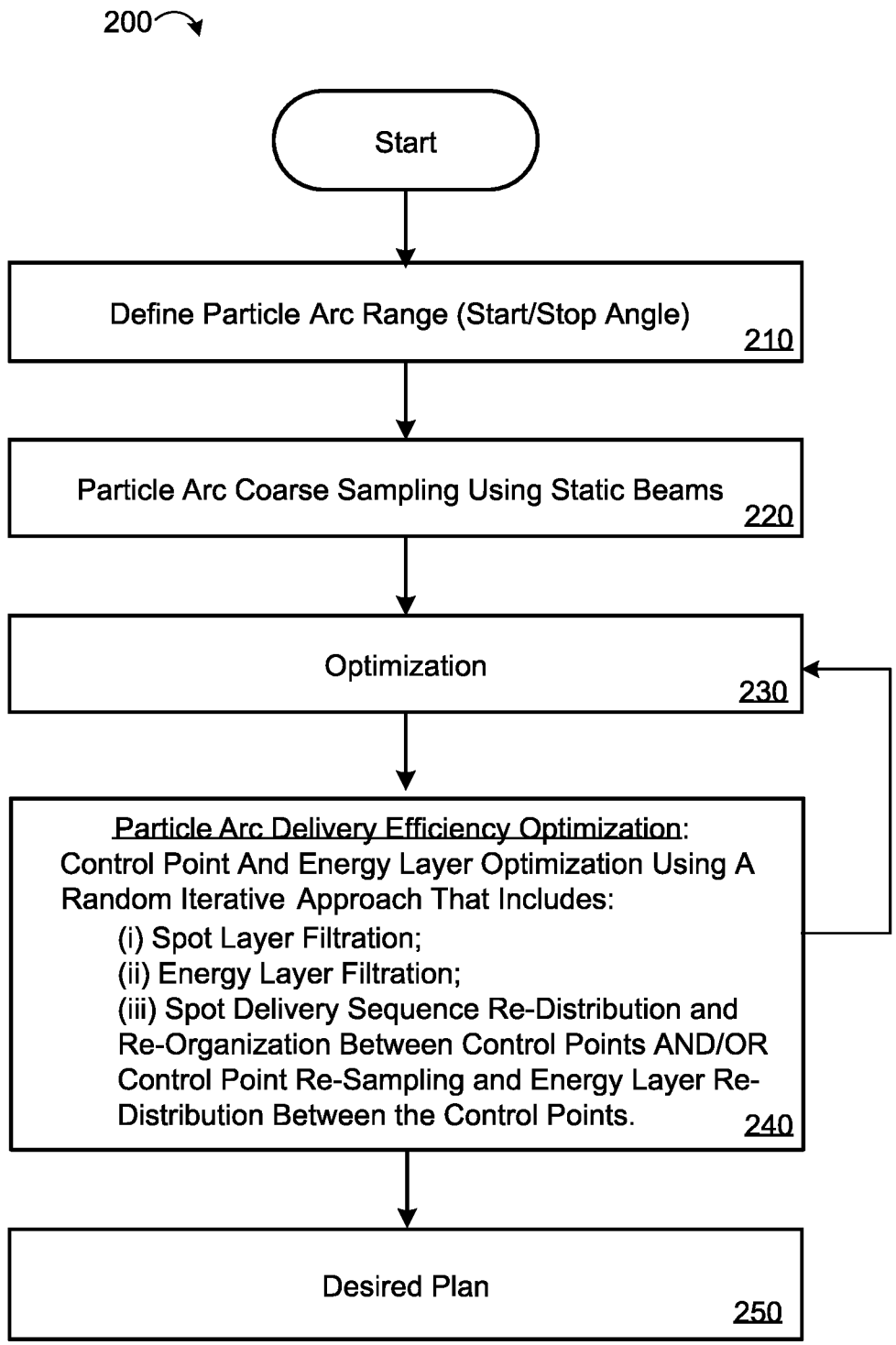
FIG. 2A is an example arrangement of operations for operating the system of FIG. 1.
Figure 2B:
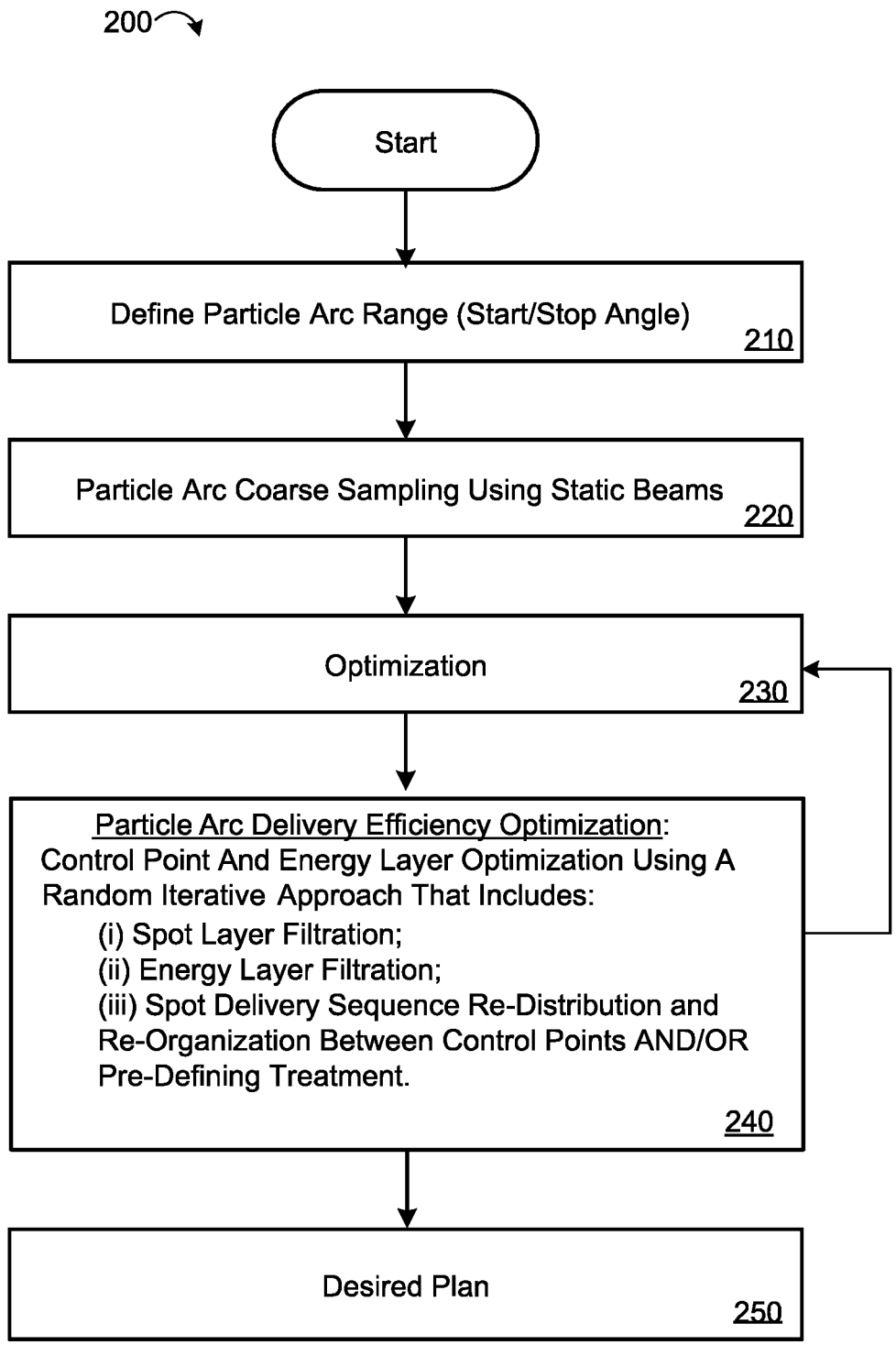
FIG. 2B is an example arrangement of operations for operating the system of FIG. 1.

Following the optional control point, energy layer optimization and spot delivery sequence optimization described about in block 240 or, instead skipping the optional optimization about (A), system 100 may be formatted to either:

(i) Re-sample the control points 124, and re-organize and re-distribute the energy layers between the control points 124 as illustrated in FIG. 2A. For example, sequential optimization can be utilized such that system 100 first increases the control point sampling frequency CPSF through control point re-sampling and energy layer re-distribution mechanism (as described above) and then employs one or both of energy layer filtration and spot number reduction mechanisms to reduce the number of energy layers and spot number per plan (as described above), and vice versa; or (ii) Allow the practitioner to identify a pre-defined control point sampling frequency (CPSF) and, based on the desired CPSF, pre-defining energy layers and performing sorting as illustrated in FIG. 2B. For example, if a practitioner defines a prostate proton arc plan having two degrees per control point (i.e., 180 control points on a 360 degree rotation axis), in order to optimize the arc plan in a reasonable calculation time and computer resources, system 100 predefines control point zones (e.g., in the prostate example, we defined 8 zones and each zone contains 20 control points). In such an example, each zone contains a range of the energy layers (e.g. 250 MeV to 70 MeV) and each control point and then assigned with a sub-predefined range e.g. control point #1 range from 250 MeV to 210 MeV, Control point #2 range from 210 MeV to 160 MeV. It can be evenly distributed or unevenly distributed. Then it followed by optimization process in which it will find an optimum plan quality based on such predefined zone and control points.

In an implementation, at block 250 system 100 generates an optimized plan for patient 112. As described, the determined plan may be tailored to accommodate a specific patient 112, and may be adjustable based on variables of patient 112 (e.g., the patient's daily treatment setup, proton range uncertainties, tumor motion, weight, the size of the tumor 114, other patient related measurements, and the like). In an implementation, system 100 includes a processor that is additionally programmed to generate, and identify, one or more alternative plans that may alternatively account for different plan parameters, plan qualities, delivery efficiencies, clinician defined variables, and the like). In an implementation, a user is able to pick one from the one or more number of plans. In an implementation, a database may be provided that includes hundreds of plans which could be based on the objective value of each plan, each individual objective function or delivery time for different machines (fix gantry, full gantry, synchrotron or cyclotron machine) or parameters (energy layer numbers, spot numbers or MU). An example graphical user interface is provided at FIG. 10 that illustrates a number of such plans in which the clinician could select.

Figure 3A:
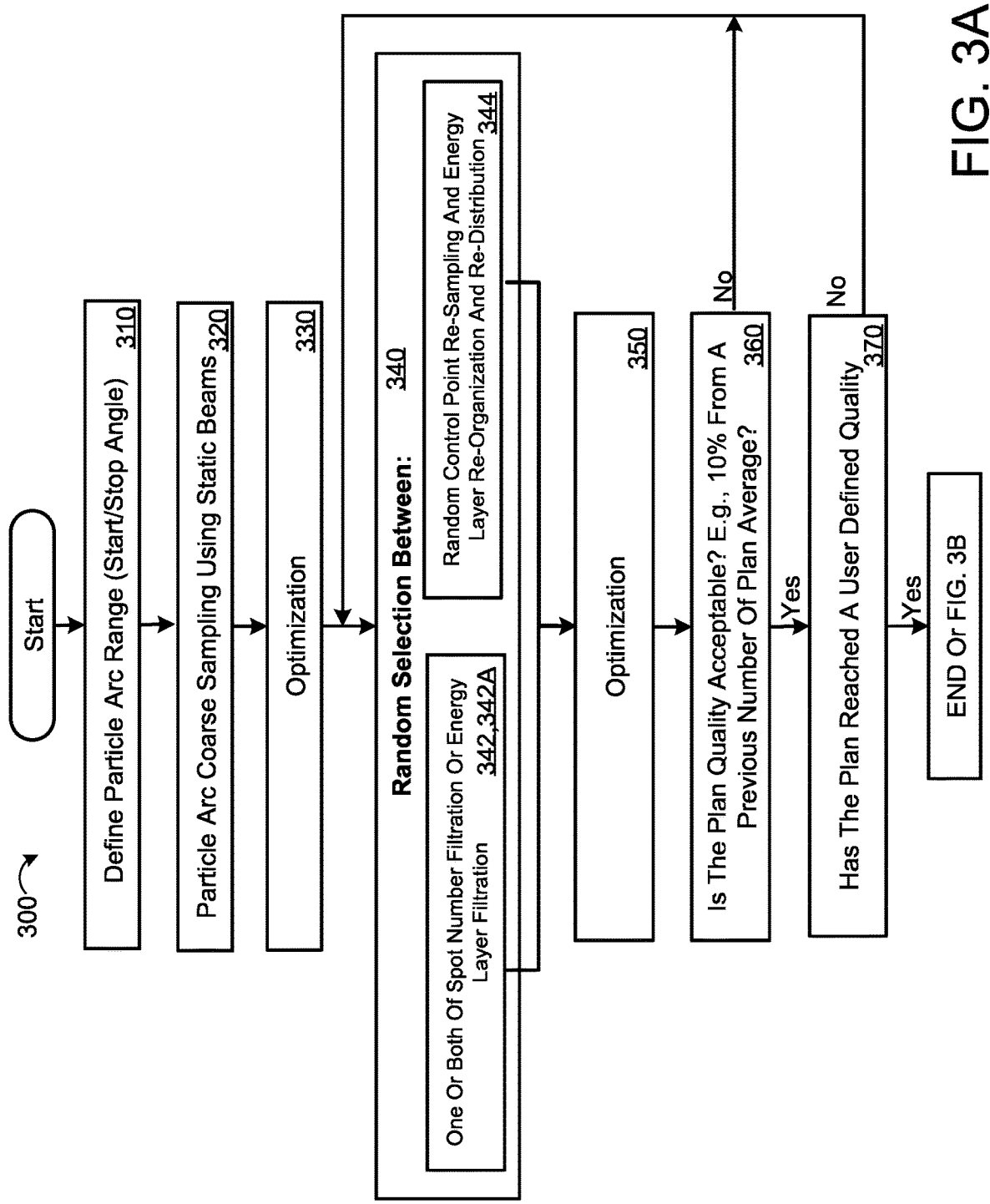
FIGS. 3A-3D illustrate exemplary arrangements of operations for operating the system of FIG. 1.
Figure 3B:
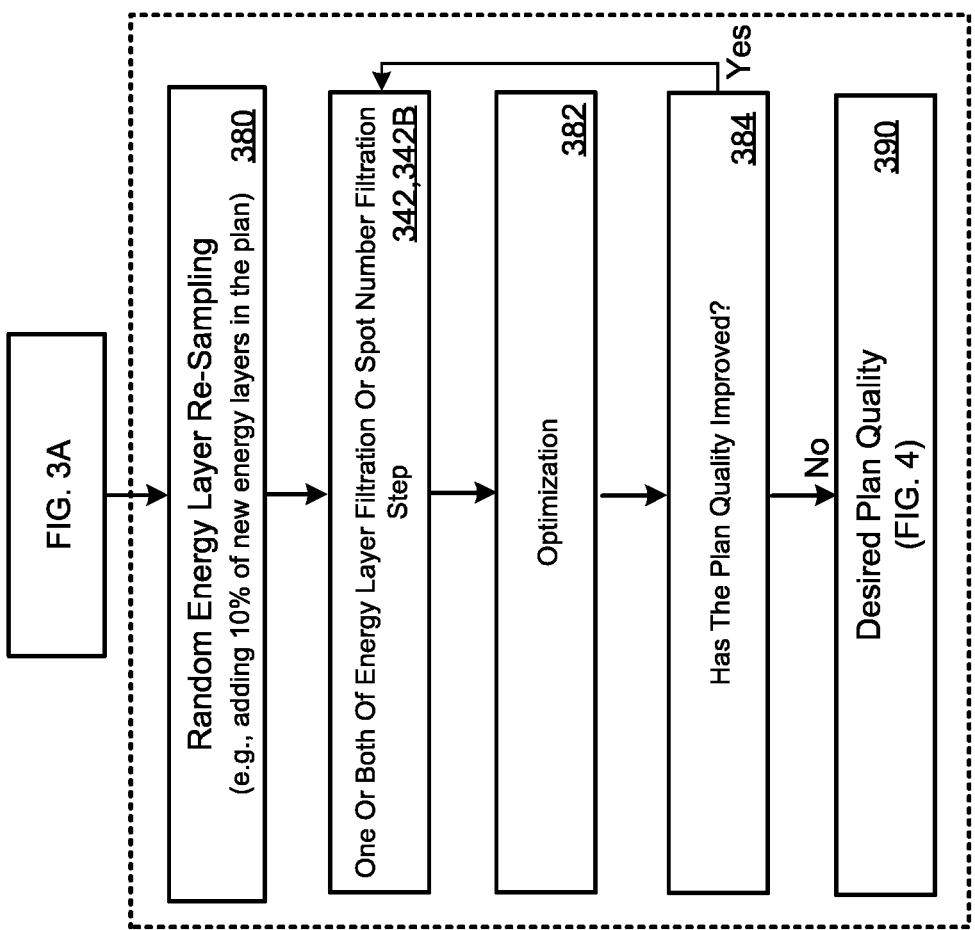

FIGS. 3A and 3B describe a more detailed example arrangement of operations than FIG. 2 for a method 300 of operating system 100. At block 310, similar to block 210 of FIG. 2, system 100 defines a proton arc range (i.e., the initial angle $\alpha_i$ and stop angle $\alpha_s$ of output 120 within the rotation of gantry and/or couch 110 (see FIG. 4A)). For example, system 100 sets an initial angle $\alpha_i$ as the initial control point 124 (i.e., gantry location) of output 120 emitting beam 104. In some implementations, system 100 also sets a table initial angle for the table 110. Therefore, in some implementations, system 100 defines an initial angle $\alpha_i$ for output 120 and/or a table initial angle for table 110, such that beam 104 from output 120 is capable of reaching tumor 114 at the desired impact angle IA. The operating system could deliver multi-iso center particle beam therapy or non-coplanar multi-isocenter particle beam with couch/table and gantry movements.

At block 320, similar to block 220 of FIG. 2, system 100 determines a coarse control point sampling, as shown in FIG. 4A, between the identified initial angle $\alpha_i$ and the identified initial stop angle $\alpha_s$. In other words, system 100 identifies a set of gantry and/or couch locations or control points 124 between the identified initial angle $\alpha_i$ and the identified initial stop angle $\alpha_s$. As shown in FIG. 4, system 100 identifies eight control points 124 within the gantry's 360-degrees. In this example, the initial angle $\alpha_i$ is at zero degrees and the initial stop angle $\alpha_s$ is at 360 degrees. Other numbers of sampling control points 124 between the initial angle $\alpha_i$ and the initial stop angle $\alpha_s$ are possible as well.

Referring back to FIGS. 3A and 3B, at block 330, system 100 determines an optimization treatment plan for patient 112 that determines a beam dose plan used by beam 104 at the identified control points 124 (identified at block 320) to irradiate tumor 114 similar to the optimization treatment plan described above with respect to block 230 of FIG. 2. In some examples, data processing hardware 130 executes the optimization of the treatment plan based on information stored on the memory hardware in communication with the data processing hardware 130. The optimization may include one or more optimization techniques or methods, such as but not limited to, robust optimization, four or five-dimensional (time and geometry change or frequency dimension) robust optimization, adaptive optimization, and radiation biological effect (RBE) optimization. The optimization treatment plan includes identifying an energy layer associated with a beam, a spot position, and a number of protons to be delivered in each beam 104 originating from output 120 at the identified control points 124 (identified at block 320). In addition, system 100 determines the optimization treatment plan for patient 112 at the identified control points 124 by considering the anatomy of the patient 112. In addition, system 100 optimizes a dose distribution in patient 112 (for example, by considering daily treatment setup and proton range uncertainties), which allows a robust dose distribution to the tumor as well as spare the healthy tissue and organs under these uncertainties. In some implementations, system 100 determines the effects of potential changes to tumor 114, for example, and adjusts the treatment plan accordingly, which may be referred to as treatment plan adaptation. Some changes may include the patient gaining or losing weight, the tumor changing size, or other considerations. By using robust optimization, system 100 is capable of providing optimal robust target coverage while sparing healthy tissue.

At block 340, system 100 optionally randomly selects between an energy filtration method at block 342, 342A and a control point re-sampling, energy layer re-distribution method and spot delivery sequence re-distribution at block 344. At optional block 342A, system 100 filters the energy layers of beam 104. In other words, system 100 removes low-weighted energy layers associated with one beam or the total beams associated with the treatment plan. System 100 may define a cut off MU weighting threshold for one or both of the energy layers or the spot numbers, so that the energy layers or spot numbers fail to meet the cutoff threshold will not be further considered at later steps of the method. For example, system 100 identifies the lowest 10% of MU weighting energy layers associated with all control points 124 and removes the identified lowest 10% of energy layers associated with all the control points 124. Other cutoff percentages may be used as well. In other examples, the MU weighting threshold for the energy layer may be associated with beams 104 outputted at each control point.

Figure 3C:
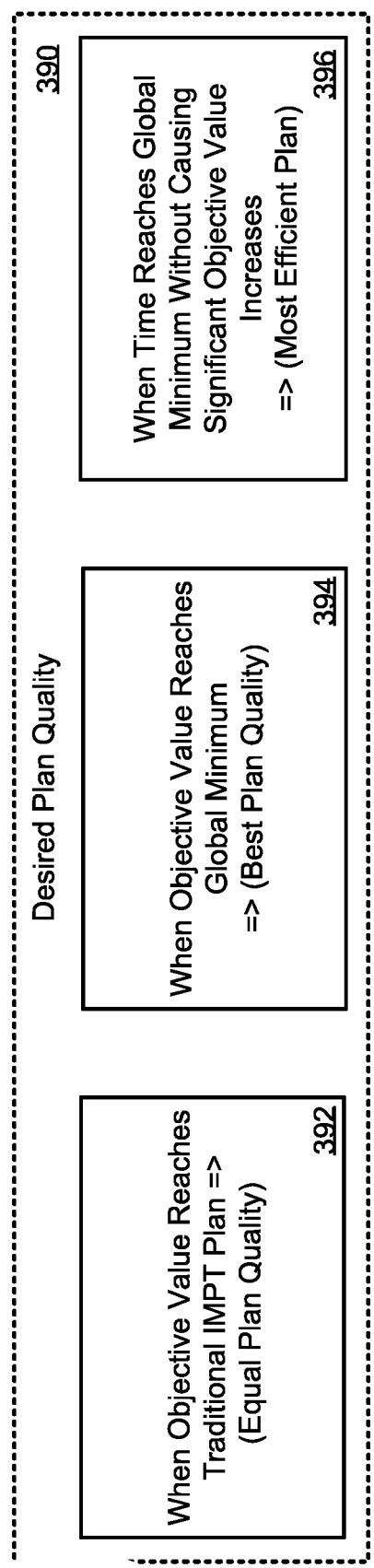
Figure 3D:
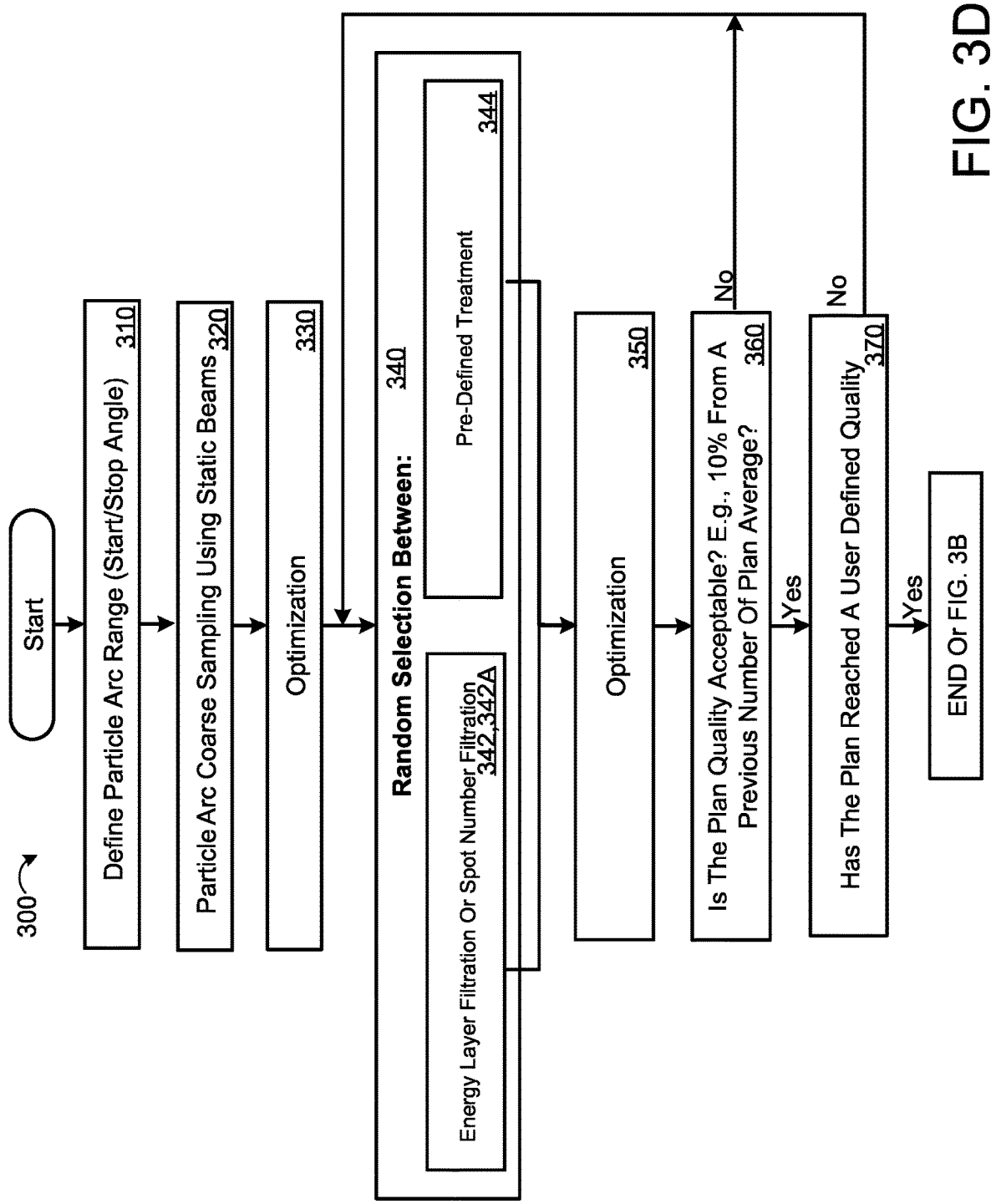

As previously discussed, at block 340, system 100 may either (i) randomly select between the energy filtration method at block 342A and the control point re-sampling, energy layer re-distribution and spot delivery sequence re-organization method at block 344 (as illustrated in FIGS. 3A-3C) or (ii) allow the practitioner to identify a pre-defined control point sampling frequency (CPSF) and, based on the desired CPSF, pre-defines energy layers and perform sorting based on the particular treatment (as illustrated in FIG. 3D).

If system 100 selects the control point re-sampling, energy layer re-distribution and spot delivery sequence method at block 344, then system 100 filters one or both of the energy layers or the spots associated with beams 104 of the treatment plan.

In an implementation, system 100 re-samples the control points 124, or more specifically increases the number of control points as shown in FIGS. 4B and 4C. FIG. 4B illustrates a method that system 100 uses to split a control point 124 into first and second control points 124 (1a and 1b), while FIG. 4C shows a method used by system 100 to add a control point 124 (e.g., adding control point 2). While certain splitting methods are disclosed, other splitting methods may be employed and the disclosure should not be so limited.

FIG. 4B illustrates an implementation of a first control point 1, 124 split into two new control points 1a, 1b, 124, each having a position different from the position of the first control point 1, 124, for example, adjacent to the first control point 1, 124, such as, on either side of the first control point 1, 124. In some examples, the first control point 1, 124 may be split into more than two control points 124, e.g., three or more. Additionally, referring to FIGS. 5A-5C, the energy layer(s) (EL) associated with a control point 124 are re-distributed and re-organized. For example, the first control point 1, 124 is capable of emitting beams 104, where each beam has an energy layer EL from the energy layers EL1-ELn. Each energy layer EL1-ELn is optimized to deliver a robust proton treatment therapy to the patient 112 and ensure a robust tumor coverage as well as sparing organs that are not cancerous. In some examples, the energy layers EL1-ELn are arranged in ascending/descending order where the first energy layer EL1 associated with a first beam 104 has less energy than the last energy layer ELn associated with a different beam 104. In other words, the different beam 104 having the last energy layer ELn (highest energy layer) reaches the furthest distance within the tumor 114. The first control point 1, 124 is split between a first new control point 1a, 124 and a second new control point 1b, 124. As shown, system 100 splits the energy layers EL1-ELn of the first control point 1, 124 by consecutively giving each one of the first and second new control points 1a, 1b, 124 energy layers EL1-ELn of the first control point 1, 124. Therefore, once all the energy layers EL1-ELn of the first control point 1, 124 are split between the first and second new control points 1a, 1b, 124, then the first new control point 1a, 124 has a number of energy layers $N_{EL(1a)}$ calculated according to:

$$N_{EL(1a)}=(N+1)/2 \text{ if } N \text{ is odd} \quad (1A)$$

$$N_{EL(1a)}=N/2 \text{ if } N \text{ is even} \quad (1B)$$

where N is the total number of energy layers EL of the control point 1, 124 prior to being split. In addition, the second new control point 1b, 124 has a number of energy layers $N_{EL(1b)}$ calculated according to:

$$N_{EL(1b)}=(N-1)/2 \text{ if } N \text{ is odd} \quad (2A)$$

$$N_{EL(1b)}=N/2 \text{ if } N \text{ is even} \quad (2B)$$

In some implementations, an MU associated with a beam at the first control point beam 1, 124 for a specific energy layer i may be determined by:

$$\text{Beam 1old}=\Sigma_N^1 \text{oldMUweighting}(i)*\text{EnergyLayer}(i) \quad (3)$$

where i is an energy layer EL, and N is the total number of energy layers.

After splitting the first control point 1, 124, each of the first and second new control points 124 has a beam energy calculated based on the following equations when N is even:

$$\text{Beam } 1a=\Sigma_{i=0}^{N/2-1}\text{oldMUweighting}(2i+1)*\text{EnergyLayer}(2i+1) \quad (4A)$$

$$\text{Beam } 1b=\Sigma_{i=}^{N/2}\text{oldMUweighting}(2i)*\text{EnergyLayer}(2i) \quad (5A)$$

The beam energy for the first and second new control point 124 may be calculated based on the following equations when N is odd:

$$\text{Beam } 1a=\Sigma_{i=0}^{(N-1)/2}\text{oldMUweighting}(2n+1)*\text{EnergyLayer}(2i+1) \quad (5A)$$

$$\text{Beam } 1B = \sum_{i=0}^{(N-1)/2} \text{oldMUweighting}(2n)*\text{Energy-Layer}(2i+1) \tag{5B}$$

where N is the total number of the energy layer.

In an implementation, system 100 employs a spot number (weighting) mechanism in addition to, or separately from, the energy layer filtration as described above. The spot number or weighting reduction mechanism may be utilized to filter, or otherwise remove, the MU spots or lines sequentially designated as being below a certain threshold. It is to be appreciated that this filtration may occur simultaneously, or randomly, during the optimizations. In exemplary implementations, the threshold may be determined as a bottom ten percent (10%) after energy layer filtration, integrated with energy layer filtration, or independent of energy layer filtration.

In an implementation, system 100 may be designed to undertake energy layer re-connection to reduce or increase the number of energy layers and the associated switching time. For example, and among others, system 100 adjusts the energy layer from a first beam impact angle (IA) to the same energy level when an adjacent impact angle (IA) has (i) an energy difference that is below a threshold level, and (ii) a comparable MU weighting. For example, consider 115 MeV and 10 MU when the first impact angle (IA) is 0 degrees, and 110 MeV and 5 MU when the adjacent impact angle (IA) is 1 degree. In this instance, the energy layers of 110 MeV may be adjusted to 115 MeV so the system reduced one (1) energy layer switching time during the proton beam delivery.

FIGS. 6A-6C illustrate another example of splitting the energy layers 124 associated with a control point 1, 124, which may include for each energy layer (EL), dividing the MU associated with that energy layer EL between a first and second new control point 1a, 1b, 124 based on a threshold MU (e.g., a fraction of the MU associated with the original control point 1, 124) associated with each one of the first and second new control points 1a, 1b, 124. For example, an energy layer $EL_1$-$EL_n$ of a first control point 124 has a first MU value. The MU value may be split between the first new control point 1a, 124 and the second new control point 1b, 124, where each of the first and second new control points 1a, 1b, 124 is associated with a fraction $f_a$, $f_b$ of the MU value associated with the energy level $EL_1$-$EL_n$. The summation of the fractions $f_a$, $f_b$ equals to one ($f_a+f_b=1$). In other words, the first new control point 1a, 124 may have a first fraction $f_a$ of the energy layer $EL_1$-$EL_n$ and the second new control point 1b may have a second fraction $f_b$ of the energy layer $EL_1$-$EL_n$. For example, the energy level $EL_1$-$EL_n$ may have an MU value of 120 MU. After splitting the energy level $EL_1$-$EL_n$ into the first new and second new energy levels 1a, 1b, 124, then the $EL_1$-$EL_n$ energy level $EL_1$-$EL_n$ may having a first fraction $f_a$ being half the MU value of the MU of the energy layer $EL_1$-$EL_n$, while the second new control point 1b, 124 has an energy layer having the remaining half of the MU value of the MU of the energy level $EL_1$-$EL_n$. As such, the total number of energy layers of the first and second new control points 1a, 1b, 124 are doubled; however, the total MU of the first and second new control points 1a, 1b, 124 is equal to the MU associated with the old control point 1, 124. Therefore, if the energy level $EL_1$-$EL_n$ has an total MU of 120 MU, then the first control point 1a, 124 may have an MU of 60 MU and the second control point 1b, 124 has an MU of 60 MU. If the energy level $EL_1$-$EL_n$ has an MU of 120 MU, then the first control point 1a, 124 may have an MU of 40 MU (where $f_a$ is ⅓) and the second control point 1b, 124 has an MU of 80 MU (where $f_a$ is ⅔).

In another implementation, the system may use a combination of both the energy split such as re-distribution together with employing a split of the MU weighting of each energy mechanism.

Referring back to FIGS. 4C and 7A-7C, in some implementations, a second control point is added in addition to an original first control point, where the first control point 1, 124 remains in the same location and the second control point 2, 124 has an adjacent location to the first control point 1, 124. In some examples, more than one control point 124 is added to the first control point 1, 124, e.g., a third or more control points may be added. Referring to FIG. 4C, a second control point 2, 124 is added in addition to the first control point 1, 124. FIGS. 7A-7C illustrate the energy layer $EL_1$-$EL_n$ re-organization and re-distribution process. FIG. 7A illustrates an original first control point 1, 124 that includes energy layers $EL_1$-$EL_n$. In this case, system 100 adds a second control point 2, 124, which consecutively takes every other energy layer $EL_1$-$EL_n$ from the first control point 1, 124, which results in a first new control point 1, 124 shown in FIG. 6B, and the second control point 2, 124 shown in FIG. 7C. As a result, the new first control point 1, 124 (FIG. 7) has less energy layers $EL_1$-$EL_n$ than the original control point shown in FIG. 7A. In addition, the first new control point has a number of energy layers calculated based on equation 1, while the second new control point 2, 124 has a number of energy layers calculated based on equation 2.

In some implementations, an MU associated with the first control point beam 1, 124 for a specific energy layer i may be determined by equation 3 above. In addition, the new first control point 1a, 124 and the added control point 2, 124 have a beam energy determined by the following equations when N is even:

$$\text{Beam1new} = \sum_{i=0N/2}^{N/2-1} \text{oldMUweighting}(2i+1)*\text{EnergyLayer}(2i+1) \tag{6A}$$

$$\text{Beam 2} = \sum_{i=1}^{N/2} \text{oldMUweighting}(2i)*\text{EnergyLayer}(2i) \tag{7A}$$

if N is odd:

$$\text{Beam 1new} = \sum_{i=0}^{(N-1)/2} \text{oldMUweighting}(2i+1)*\text{EnergyLayer}(2i+1) \tag{6B}$$

$$\text{Beam 2} = \sum_{i=1}^{(N-1)/2} \text{oldMUweighting}(2i)*\text{Energy-Layer}(2i) \tag{7B}$$

where N is the total number of the energy layer.

As described in FIGS. 4B, 4C, 5A-5C, 6A-6C, and 7A-7C the energy layers EL1-ELn of a first control point 124 are split (FIGS. 4B, 5A-5C) or reduced (FIGS. 4C and 7A-7C), or its associated MU values are split (FIGS. 4B, 6A-6C) in a consecutive manner, more specifically splitting each energy layer EL to one of the new consecutive points. However, the energy layers EL associated with the first control point 1, 124 may be split in other ways, such as, but not limited to, the MU associated with each energy layer EL of the control point, a total value of MUs per control point, a total number of energy layers EL associated with each control point 124, or any other method.

It is emphasized that any method to re-organize and re-distribute the energy layers EL may be used, that the number of energy layers may not be maintained, i.e., one or more additional energy layers could be added as a re-sampling mechanism in block 362. Similarly, in some examples, each energy level within a control point may be split differently than another energy level within the same control point. In some examples, energy layer will go through a sorting process that higher energy layer moving to control point 1 and lower energy layers moving to control point 2.

Figure 8A:
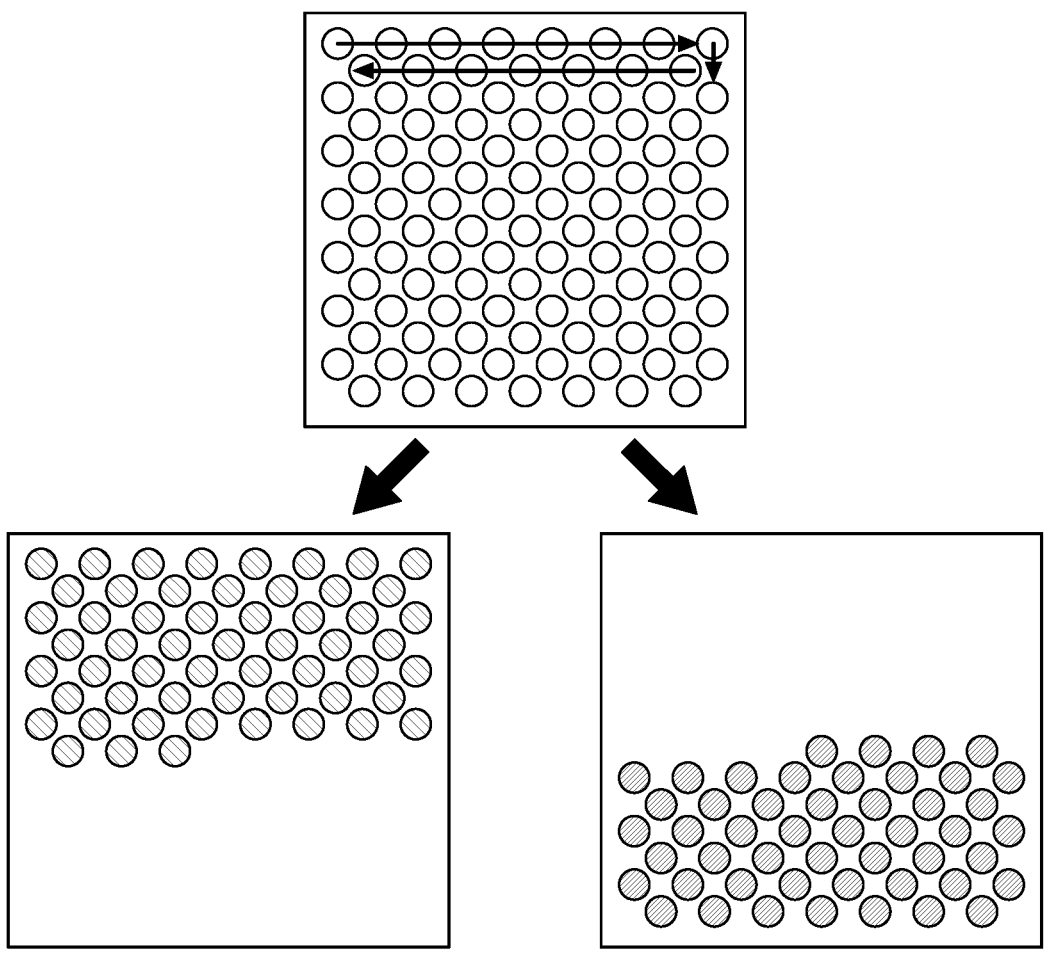
FIGS. 8A and 8B are schematic views of an example of a spot delivery sequence re-organization and interpolation technique that may be used between the control points.
Figure 8B:
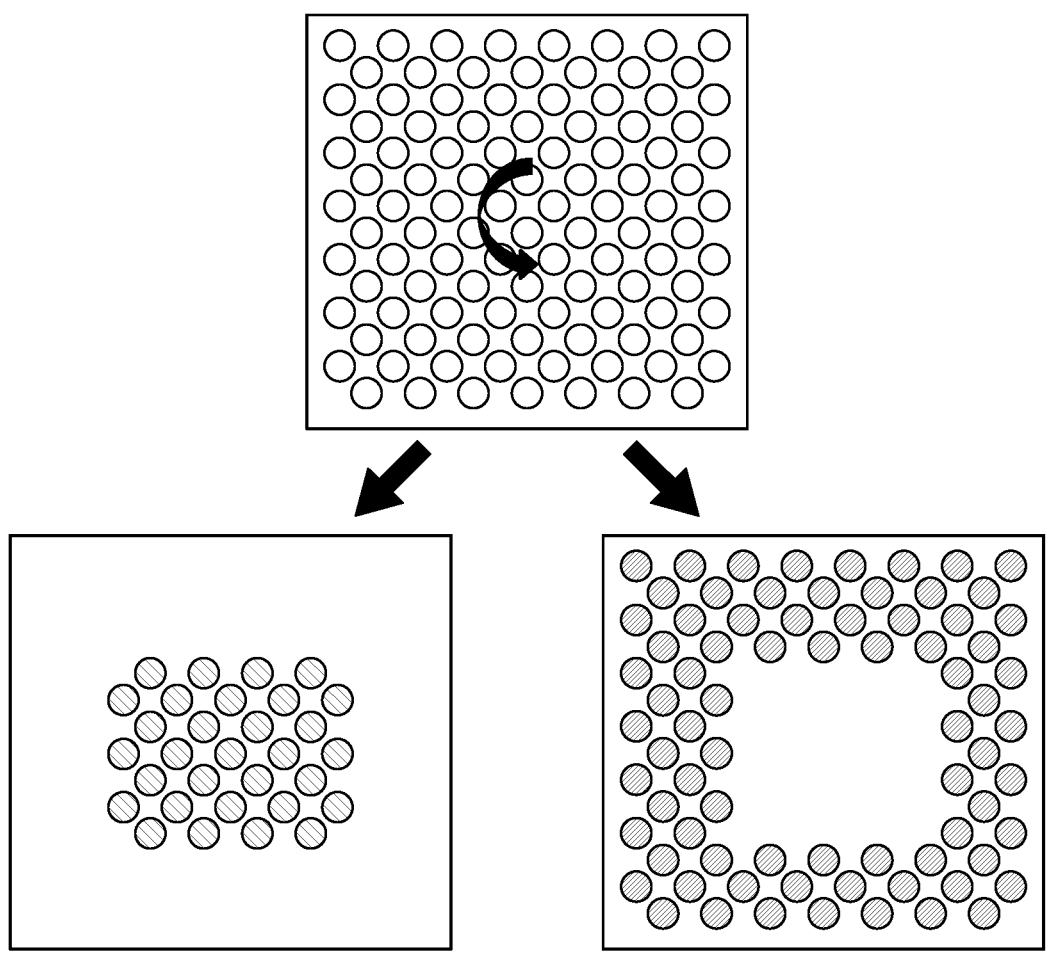
Figure 9:
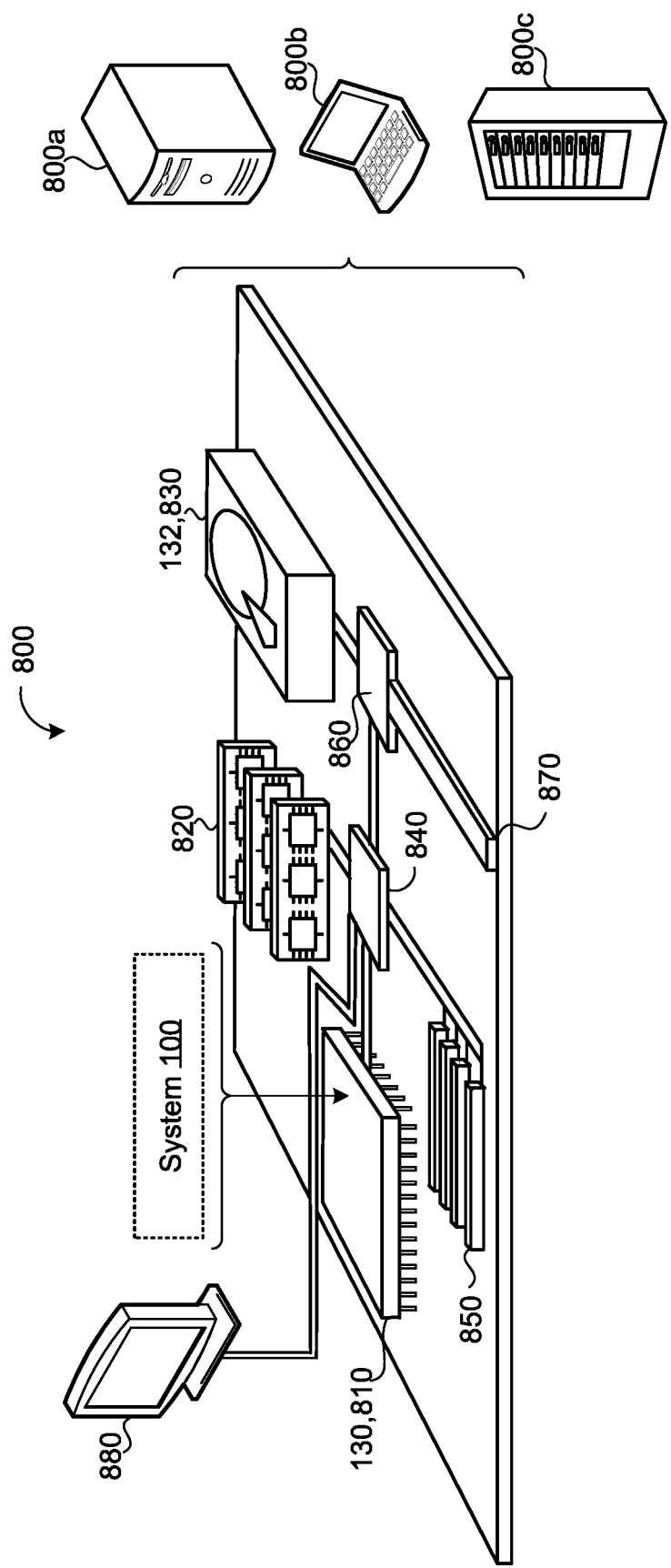
FIG. 9 is a schematic view of an example computing device executing any systems or methods described herein.

FIGS. 8A and 8B illustrate an exemplary implementation of a method to enhance a spot delivery sequence to thereby undertake a re-organization and re-distribution of a first control point (e.g., having a gantry angle 40°). As illustrated in each of FIG. 8A and FIG. 8B one or more control points 124 may be divided into two or more control points (e.g., gantry angles of 39° and 40° or couch position of x=10 cm and 10.5 cm) wherein the resultant, divided control points each have a position or gantry angle that is different from the position of the control point from which the division occurred, 124. In an implementation, for example, the divided control points may be positioned adjacent to the first control point, 124, such as, on either side of the first control point, 124. In another example, the first control point, 124 may be split into more than two control points 124, e.g., three or more. In addition to the energy layer re-distribution and re-organization such as FIGS. 5A-5C, each control point, 124, might contain multiple energy layers; such that each energy layer contains a layer of spots and further wherein each spot has a position in an X, Y direction (as referenced from the beam eye view).

An example of a sequence re-organization and re-distribution will now be described. In an implementation, the control point, 124 is capable of emitting beams 104, wherein at least one of the emitting beams has energy layer(s) EL. In the described example, each energy layer $EL_1$-$EL_n$ may be directed to one or more spots which may be, in a preferred form, optimized to deliver a robust proton treatment therapy to the patient 112 (e.g., to help ensure robust tumor coverage, spare organs that are not cancerous, and the like). It is to be appreciated that the control point splitting can be used in a variety of environments, including line scanning sequence particle therapy machines as shown in FIG. 8A and spiral scanning sequence particle therapy machines as shown in FIG. 8B. In each of FIGS. 8A and 8B, the spots of the specific energy layer illustrated with respect to the first control point, 124 are divided into first and second new control points based on the machine delivery sequence. Accordingly, the radiation dose delivered from control point that was divided is approximately equal to the aggregate radiation dose that is delivered by first and second control points. The position or gantry angle of the first and second control points is so close relative to first and second control point such that the proton beam delivered through the continuous arc delivery approximately equals the proton beam had it been delivered at the position of the static control point from which first and second control points were derived. Accordingly, the result of the described re-distribution and re-organization from a primary control point divided into two or more sub-control point is interpolation of the energy and spot delivery sequence for a continuous and dynamic particle arc treatment. For clarity, the division of the control points may include, energy layers, spots, or a combination of energy layer and spot delivery sequence re-organization and re-distribution. And, for greater clarity, the foregoing re-organization and re-distribution technique may be incorporated at one or both of the treatment plan system to optimize the plan and in the hardware (e.g., by the gantry, beamline, cyclotron, or the like) in each case to deliver an efficient and effective particle arc therapy.

In an implementation, blocks 342A and 344 may be implemented randomly for example, implementing block 342A one or more times than implementing block 344 one or more times, or implementing block 344 one or more times than implementing block 342A one or more times. The two blocks 342A and 344 are interchangeable and their interchangeability does not affect the treatment plan. However, the interchangeability of the two blocks 342A and 344 may affect the calculation time/speed for determining the treatment plan. For example, when system 100 executes block 342A first, the system 100 filters or removes low-weighted energy layers in the plan, which results in less energy layers and spots compared to when system 100 re-samples the control points 124 at block 346 first. More energy layers and spots take more time to calculate and optimize. Therefore, when system 100 executes block 344 before block 342A, it might take the system 100 longer to find a plan than when the system 100 executes block 342A before 344. For example, assuming there are eight control points each having 50 energy layers and 1500 spots, then if system 100 executes block 342A first, the result will remain eight control points 124 with 40 energy layers and 1200 spots, which is less energy layers and spots than the original plan. Then system 100 executes block 344 and re-samples the control points 124, where each control point has less energy layers than the original control points prior to filtration. However, if system 100 re-samples (block 344) the control points 124 prior to filtration (block 342A, then system 100 has to perform calculations on a larger number of energy layers and spots, which increases the time to determine an optimization treatment plan.

In an alternative system, block 340 of FIG. 3A may be obviated and replaced with a user pre-defined treatment plan identified by a user (See FIG. 3D). For example, a practitioner may identify a pre-defined control point sampling frequency (CPSF) and, based on the desired CPSF, system 100 may process this information to pre-define energy layers and performing sorting of the control points to identify a plan.

At block 350 (similar to block 330), system 100 determines an optimized treatment plan for patient 112 (e.g., a robust optimization or other types of optimizations described with respect to block 330). The optimization plan determines a beam dose plan for the beam 104 to irradiate the tumor 114. This optimization plan is based on the filtered energy layers of block 342A or the random control point re-sampling and energy layer re-organization and re-distribution at block 344. Therefore, the robust optimization at block 330 is different than the robust optimization of block 350, because each is based on the sample of control points 124 having different energy layers, e.g., the optimization at block 330 is implemented on the control points 124 having the identified energy layers, while the robust optimization at block 350 is implemented on the control points 124 having the filtered energy layers or resampled and reorganized energy layers or filtered spots.

As depicted and in some implementations, at block 360, system 100 determines if the current plan quality is acceptable. Several methods may be used to determine if the plan quality is acceptable. For example, system 100 may determine if a current plan has reached target coverage or if an objective value is reached. For example, system 100 may consider a good quality plan to include a specific number of control points 124 within the arc rotation. Therefore, an acceptable plan quality may be identified when a plan has reached a threshold number of control points 124. In other examples, a good plan quality may be identified when the plan has reached a specific proton beam delivery time that a user has defined.

In some implementations, plan quality may be assigned an objective value based on one more factors associated with a plan and a plan may be identified as a quality plan provided that the objective value is at or above an identified threshold object value. For example, system 100 may determine if an objective value associated with the treatment plan has increased, e.g., by 10% from a previous objective plan and identify whether this increase is acceptable.

In some examples, the previous objective value is an average of one or more individual objective values. In an implementation, the objective value may be a measurement of time for the cancer treatment plan to be completed. The objective value may be other values as well. If the objective value has not increased by a threshold value (e.g., 10%), then system 100 repeats blocks 340-356 until the objective value has increased by the threshold value. For example, the objective value may be a measurement of time for the cancer treatment plan to be completed. The objective value may be other values as well. If the objective value has not increased by a threshold value (e.g., 10%), then system 100 repeats blocks 340-360 until the objective value has increased by the threshold value. The objective value may be determined based on an objective function, also referred to as an optimization function and cost value, shown in the below equation:

$$\text{cost value}(F) = w_{Target} * F_{Target} + w_{Risk1} * F_{Risk1} + w_{Risk2} * F_{Risk2} \quad (8)$$

Where $w_{target}$ is a weight value associated with the target (i.e., tumor), penalties value, or an importance factor, and $F_{target}$ is the difference between the current value vs. the goal that system 100 is aiming to reach, costlets, or indicators. $w_{Risk1}$ is a weight value associated with the tissue or organs that are adjacent to the tumor; and $F_{Risk1}$ is the difference between the current dose would be delivered to the specific organs vs the goal that system 100 is aiming to spare for this specific organs.

In some examples, $F_{target}$ may be written as: $F_{Target} = (D_{target} - D_0)^2$ where $D_{target}$ is the goal of prescription dose to the target and $D_0$ is the current dose to the target. The bigger difference between the current value and objectives, the higher the cost value is, which also means the system need to further optimize the treatment plan to reach an optimized treatment plan.

In step-and-shoot mode, system 100 determines if the time for the gantry or couch rotation or translational movement, i.e., the rotation of output 120 with respect to table 110 is greater than the time to switch energy layers, then system 100 keeps at least one energy layer per control point 124, e.g., (1-6 energy layers per control point 124). For example, if it takes three seconds for gantry to move between two consecutive control points 124, and energy layer switching time is less than 3 seconds, then system 100 keeps at least one energy layer per control point 124. In an implementation of the continuous delivery mode, system 100 may optionally retain the control point resampling until it reaches a desired arc sampling frequency or process as set out in a pre-defined manner (see, e.g., block 240 in FIG. 2).

As previously discussed, higher control point sampling frequency indicates a smaller angle difference between the adjacent control points. In this situation, delivery of a beam 104 simultaneously with the gantry/couch rotation is a close approximation to delivering a beam 104 at a static control point angle. Desired arc sampling frequency means that there is enough control points within an arc so that there is almost no dosimetric difference between static step-and-shoot delivery and continuous delivery mode. Reaching a desired arc sampling frequency means that to achieve enough sampling control point so there is minimum dosimetric difference between static step-and-shoot deliveries and continuous proton beam arc delivery.

In a system 100 that utilizes an iterative optimization approach based on the random control point re-sampling, energy layer, spot delivery sequence re-organization, re-distribution, and energy layer filtration and spot number reduction. During the random iterative optimization process, each step may be arranged to generate a plan with an objective value. And once the objective value has exceeded a pre-defined threshold value, system 100 may reject the previous step and restarts the random process again. In some implementations, the optimization process includes, but is not limited to, radiobiology (RBE) optimization, physical dose optimization, and the like. For example, as illustrated in FIG. 3B, after system 100 filters the energy layers at block 342A or re-samples the control points 124 and re-organizes and re-distributes the energy layers at block 344, 350A, if the objective value is higher than 10% of the previous plan, the current filtered or re-sampled new control points will be rejected and the system 100 starts a new random search procedure based on the previous plan. If the objective value is lower than the previous plan, system 100 accepts the new filtered or re-sampled control points 124 and continues the random search based on the current plan.

At block 370, an implementation of a system 100 may determine if a treatment plan has reached a user defined quality based on user preference, such as, e.g., a specific time, tumor coverage, or other measurable variables. If system 100 determines that the treatment plan has not reached the user defined quality, then system 100 reiterates block 340, described above by selecting a random method between the energy layer filtration at block 342A or the control point re-sampling and energy layer re-distribution at block 344. System 100 repeats this process until system 100 determines that the treatment plan reached is according to the user defined plan quality. Once, system 100 determines that the treatment plan reached is according to the user defined plan quality, system 100 can begin treatment of the tumor 114 according to the plan. System 100 randomly repeats blocks 342A and 344 as long as the treatment plan has not reached a user defined quality to increase or split the original coarse sampling control points (shown in FIG. 4A) into new and finite control points without causing unacceptable plan and dose calculation time, resulting in a step-and-shoot or a continuous delivery arc plan with desired control point 124 sampling frequency. Therefore, system 100 seeks to create enough sampling control points or a sampling rate for a continuous arc delivery. This results in a significantly reduced calculation time. For example, system 100 may deliver a beam 104 having at least one energy layer (e.g., 1-6 energy layers each outputted at as a separate beam) at each control point 124, where system 100, after executing blocks 342A and 344 determines that the SPArc includes 360 degrees of full rotation about the patient, with control points at every two degrees. In other words, system 100 delivers a beam 104 to the patient 112 at every two degrees or continuously delivers the beam during the gantry/couch rotation, delivering the most efficient treatment plan.

Referring to FIG. 3B, in some implementations, system 100 performs additional optional improvements to the treatment plan of FIG. 3A. At block 380, system 100 performs random energy layer re-sampling on the previously reached treatment plan at block 370. For example, system 100 randomly adds additional energy layers to the treatment plan at random control points 124 (i.e., existing control points 124). System 100 may add an additional 10% energy layer to further optimize the treatment plan.

At block 342B, system 100 performs energy layer filtration similar to the energy layer filtration performed in block 342A. Thereafter, system 100 may perform an optimization step at block 382 that is similar to the optimization referenced at blocks 330 and 350. At block 384, system 100 undertakes to determine if the treatment plan quality has improved compared to the last plan quality. If the system 100 identifies that the treatment plan quality has improved, then system 100 determines that the treatment plan quality may be further improved and performs block 342B-384 until system 100 determines that the plan quality can no longer be improved. When system 100 determines that the treatment plan quality may not be improved, system 100 determines that it is the desired treatment plan for the patient 112.

In some examples, the desired treatment plan may be based on user pre-defined factors. Referring to FIG. 3C, at block 390, system 100 delivers an optimized and efficient cancer treatment plan with continuous beam delivery, based on one of the user preferences. For example, some clinicians prefer best plan quality, so they will choose the lowest objective value plan. Some clinicians prefer a faster delivery plan, so they might choose a plan with the shortest delivery time while compromise the plan quality. Or some clinicians will choose a moderated plan with both good plan quality as well as medium delivery time.

Traditional proton systems extract each energy layer one by one through an energy selection method. However, system 100 includes a proton system that will be able to extract multi-energy layers at same time. In this case, system 100 delivers a proton beam 104 having multi-energy layers at a control point 124 in a step-and-shoot or continuously without costing additional energy layer switch time. In energy re-distribution mechanism 344, system 100 use the methods described in FIGS. 2-6 to re-distribute the energy layer to the new control points 124.

Figure 10:
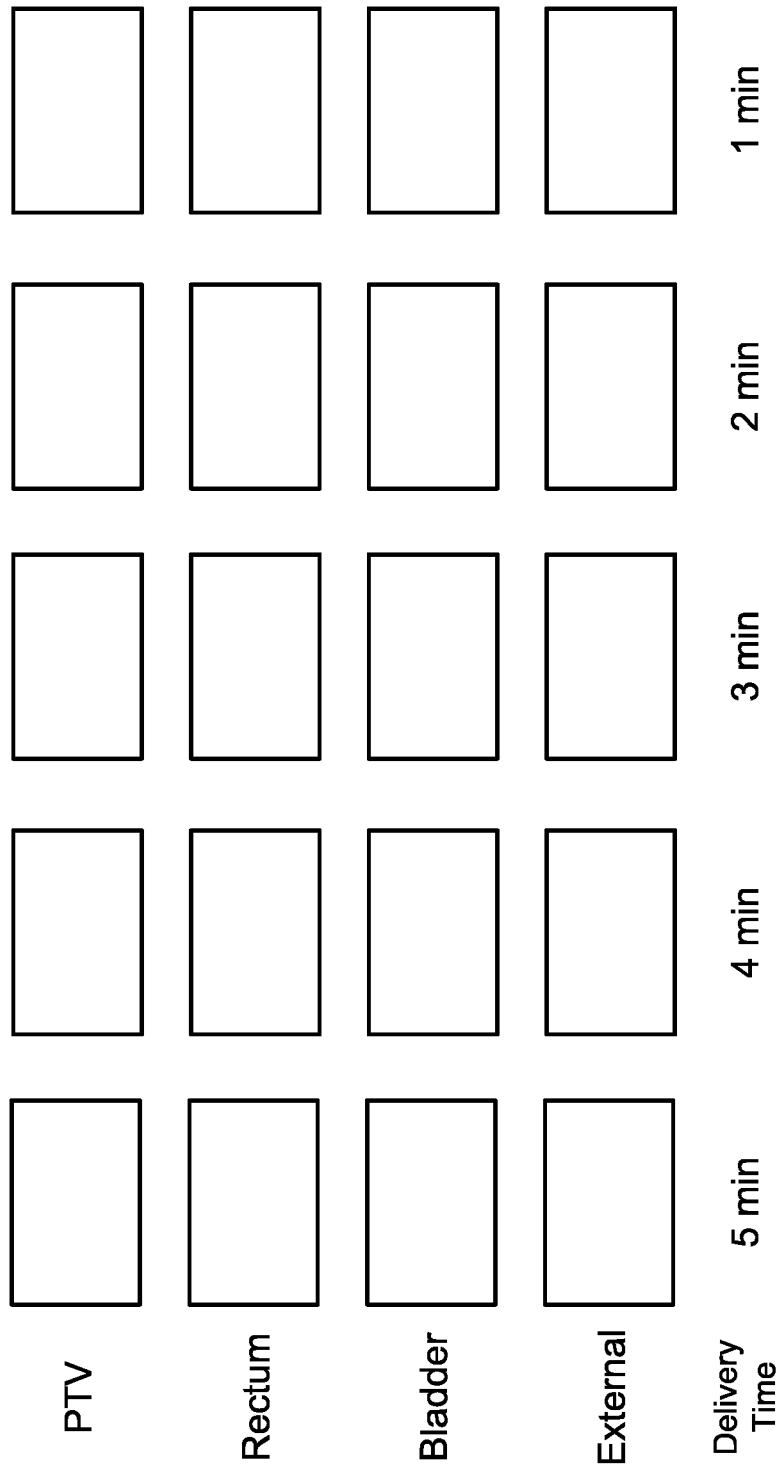
FIG. 10 is an example of a graphical user interface that illustrates plan selections for presenting to a user.

FIG. 10 is a schematic view of an example computing device 800 that may be used to implement the systems and methods described in this document. The computing device 800 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The treatment planning and delivery mechanism includes computational based optimal beam angle (step and shoot) and optimal arc trajectory (continues arc) searching software platform and delivery framework to improve overall treatment plan quality and delivery efficiency. The optimal beam angle and trajectory-searching algorithm utilizes the entire solid angle search space for treatment dose optimization to further increase the therapeutic ratio. Optimal arc trajectories are generated and selected based on global optimization of the spot positions, spot weighting, and beam angles. The most efficient arc trajectories are selected for treatment delivery.

The computing device 800 includes a processor 130, 810, memory 820, a storage device 132, 830, a high-speed interface/controller 840 connecting to the memory 820 and high-speed expansion ports 850, and a low speed interface/controller 860 connecting to low speed bus 870 and storage device 830. Each of the components 810, 820, 830, 840, 850, and 860, are interconnected using various busses, and may be mounted on a common motherboard or in other manners as appropriate. The processor 810 can process instructions for execution within the computing device 800, including instructions stored in the memory 820 or on the storage device 830 to display graphical information for a graphical user interface (GUI) on an external input/output device, such as display 880 coupled to high speed interface 840. In other implementations, multiple processors and/or multiple buses may be used, as appropriate, along with multiple memories and types of memory. Also, multiple computing devices 800 may be connected, with each device providing portions of the necessary operations (e.g., as a server bank, a group of blade servers, or a multi-processor system).

The memory 820 stores information non-transitorily within the computing device 800. The memory 820 may be a computer-readable medium, a volatile memory unit(s), or non-volatile memory unit(s). The non-transitory memory 820 may be physical devices used to store programs (e.g., sequences of instructions) or data (e.g., program state information) on a temporary or permanent basis for use by the computing device 800. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 830 is capable of providing mass storage for the computing device 800. In some implementations, the storage device 830 is a computer-readable medium. In various different implementations, the storage device 830 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 820, the storage device 830, or memory on processor 810.

The high speed controller 840 manages bandwidth-intensive operations for the computing device 800, while the low speed controller 860 manages lower bandwidth-intensive operations. Such allocation of duties is exemplary only. In some implementations, the high-speed controller 840 is coupled to the memory 820, the display 880 (e.g., through a graphics processor or accelerator), and to the high-speed expansion ports 850, which may accept various expansion cards (not shown). In some implementations, the low-speed controller 860 is coupled to the storage device 830 and low-speed expansion port 870. The low-speed expansion port 870, which may include various communication ports (e.g., USB, Bluetooth, Ethernet, wireless Ethernet), may be coupled to one or more input/output devices, such as a keyboard, a pointing device, a scanner, or a networking device, such as a switch or router, e.g., through a network adapter.

The computing device 800 may be implemented in a number of different forms, as shown in the figure. For example, it may be implemented as a standard server 800a or multiple times in a group of such servers 800a, as a laptop computer 800b, or as part of a rack server system 800c.

Figure 11:
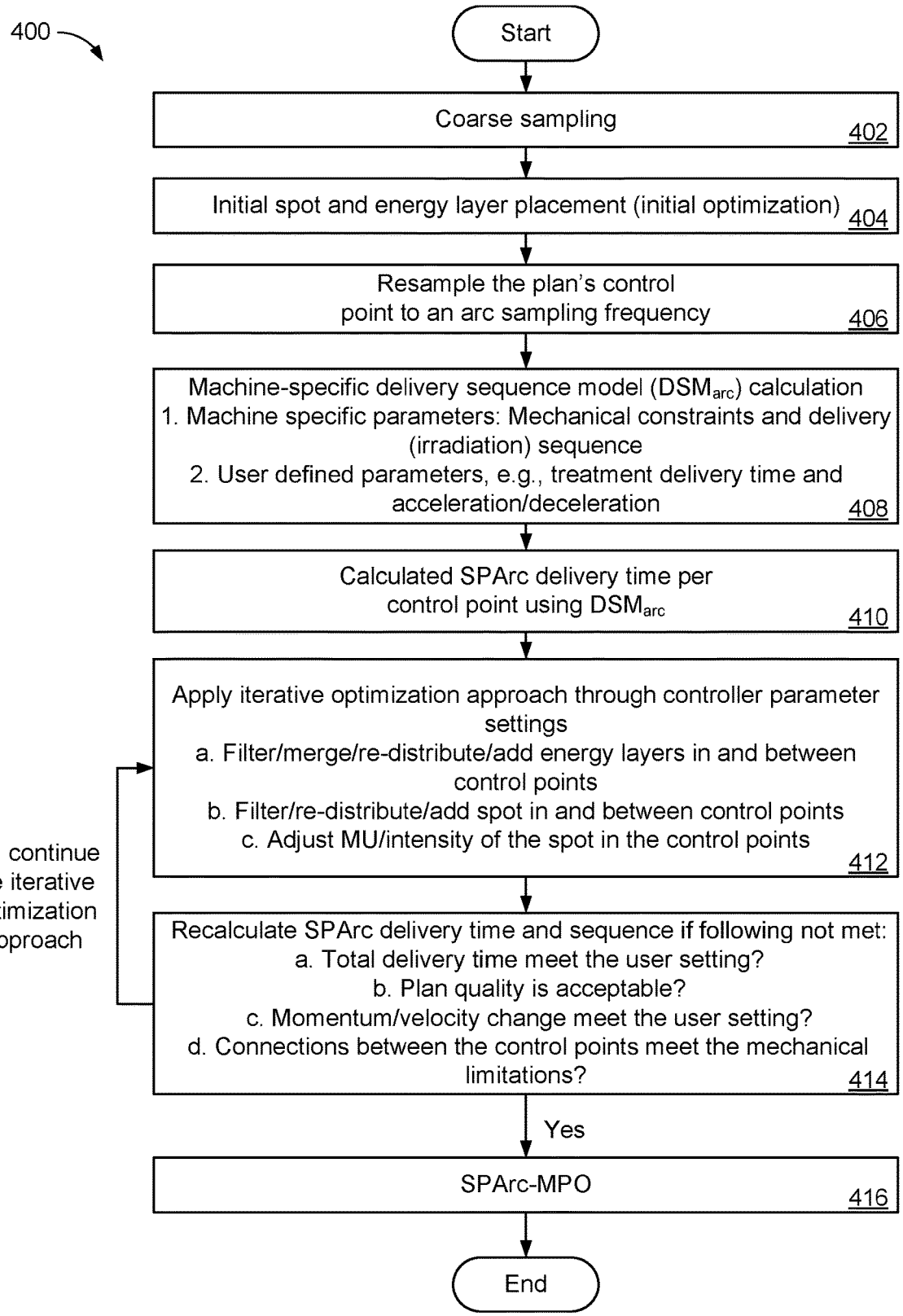
FIG. 11 is an example arrangement of operations for optimizing the operation of the system of FIG. 1.

FIG. 11 describes an example arrangement of operations for a method 400 of optimizing the operation of system 100. In some implementations, the method 400 may improve the mechanical connection between the control points 124 based on the rotation speed and acceleration of the gantry 122. In some implementations, the method 400 may quantitatively control the rotation speed and/or momentum changes of the gantry 122 during direct mechanical parameter incorporated iterative SPArc optimization (SPArc-MPO).

At block 402, coarse sampling is conducted. At block 404, an initial coarse optimization is performed to calculate and place the energy distribution, spot position, and weighting in the coarse sampling arc segments. At block 406, one or more control point may be re-sampled from a coarse frequency (e.g. 20 degree per control point) to a fine arc sampling frequency (e.g. 2 degree per control point) through the redistribution of the MU weighting, energy layers and spot number. In an implementation, and as shown on FIG. 11, this may occur through optimization of an energy layer delivery sequence sorting and redistribution mechanism (referred to as the SPArc-seq) between the control points 124, the arc sampling frequency, e.g., 1, 2, 2.5 degrees, etc., is determined.

At block 408, a machine-specific delivery sequence model ($DSM_{arc}$) may be employed to calculate the delivery time and sequence based on machine specific or proton system properties (including parameters and user defined or preferred parameters). The machine specific parameters may include mechanical parameters and electronic parameters. The mechanical parameters may include (i) a delivery tolerance window, e.g., +/−1 degree, (ii) gantry mechanical limitations, e.g., rotation speed, momentum changes, acceleration/deceleration speed, and (iii) mechanism of control point connections including a delivery window buffer and acceleration/deceleration speed to connect the adjacent control points.

Optimization of dose-volume objectives may be constrained by the machine-specific parameters that are calculated from the machine-specific delivery sequence model such as gantry speed limitation, gantry acceleration, energy switch time, and spot delivery time, where, in some implementations, the constraints may be defined as follows. The division of control point resampling frequency may be defined by the following equation:

$$\theta = \alpha + \beta \quad (9)$$

Where $\theta$ is the angle resampling frequency, $\beta$ is the tolerance window for ideal delivery, and $\alpha$ is an angle interval which is used for energy switching and gantry velocity acceleration. Gantry speed may be defined as:

$$v_i * t_i \leq \beta \quad (10)$$

Where $v_i$ is the gantry velocity during delivery and $t_i$ is the spot delivery time within the i-th control point, respectively. The constraint of gantry speed difference between the neighbor control points includes the constraint of rotation angle interval for acceleration and the constraint of accelerated time. Rotation angle interval for acceleration may be defined as:

$$(v_i^2 - v_{i+1}^2) = 2 * \text{sign}(v_i - v_{i+1}) * a * \alpha \quad (11)$$

Which means the acceleration may be accomplished within the angle interval a, a is gantry speed acceleration, and sign is the sign function. The constraint of accelerated time may be defined as:

$$v_i - v_{i+1} \leq \text{sign}(v_i - v_{i+1}) * a * ELST_i \quad (12)$$

Which means the acceleration may be accomplished within the energy switch time $ELST_i$, where ELST is the energy switch time within the i-th control point. Thus, the constraint of delta gantry speed between control point may be derived as:

$$v_i - v_{i+1} \leq \max(\text{sign}(v_i - v_{i+1}) * a(v_i - v_{i+1}), a * ELSt_i) \quad (13)$$

The velocity/momentum change constraint between the control points or during the treat delivery may be defined as:

$$V_i - V_{i+1} = \Delta V > \text{user settings} \quad (14)$$

To minimize the speed difference between the adjacent control point i and i+1, the SPArc-MPO iteratively (i) adds/deletes/re-distributes spots and (ii) merges/redistributes/deletes/adds/modifies energy layers.

The electronic parameters, such as proton spot/energy/burst/line irradiation or delivery sequence, may include (i) spot-switching time, (ii) spot drill time, (iii) energy layer switching time, and (iv) burst-switching time. The user defined parameters may include (i) a defined total SPArc delivery time/speed, e.g., 4 minutes, (ii) a delivery tolerance window, e.g., +/−1 degree (which may be equal to the machine parameter), and (iii) momentum/speed change during the treatment delivery.

At block 410, the calculated SPArc delivery time per control point 124 is implemented using $DSM_{arc}$. At block 412, the SPArc-MPO may iteratively adjust the proton beam delivery time within and between the control points 124 through (i) filtering, merging, re-distributing existing energy layers, and/or adding new energy layers, (ii) filtering, merging, re-distributing existing proton spots, and/or adding new proton spots within and between the control points 124, and (iii) adjusting the MU or intensity of the proton spots within and between the control points 124. Through the iterative SPArc optimization framework, the SPArc-MPO gradually adjusts the delivery time within and between adjacent control points 124 through direct mechanical parameters optimization to ensure a smooth and efficient rotational proton arc delivery which may fit a specific proton machine parameters such as max/min gantry speed, acceleration/deceleration speed, and controller limitation between the control points 124.

At block 414, the method 400 returns to block 412 to continue the iterative optimization approach if the following conditions are not satisfied: (i) total delivery meet the user setting, (ii) plan quality is acceptable, (iii) momentum/velocity change meet the user setting, and (iv) connections between the control points meet the mechanical limitations. If these conditions are satisfied, then at block 416, the method 400 proceeds to the SPArc-MPO.

Various implementations of the systems and techniques described here can be realized in digital electronic circuitry, integrated circuitry, specially designed ASICs (application specific integrated circuits), FPGAs (field-programmable gate arrays), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for this programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit), or an ASIC specially designed to withstand the high radiation environment of space (known as "radiation hardened", or "rad-hard").

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method of optimizing delivery of a particle beam at a target, wherein the particle beam is delivered from an output device at a plurality of control points, the method comprising:
   delivering a substantially continuous particle beam about the plurality of control points;
   iteratively adjusting a delivery time of the substantially continuous particle beam about the plurality of control points;
   identifying an initial set of control points;
   providing a first group of optimized beams, wherein each optimized beam of the first group of optimized beams is configured to be output at a first control point and steered towards one or more energy layers that are associated with one or more monitor unit (MU);
   providing a second group of optimized beams, each optimized beam of the second group of optimized beams configured to be output at the first control point and having a reduced number of energy layers;
   increasing a number of the initial control points; and
   maintaining a total number of energy layers as one of equal to, more than, or less than a total number of energy layers associated with the initial control points during movement of the beam between the plurality of control points, wherein increasing the number of initial control points comprises adding one or more adjacent control points to each initial control point, the adjacent control point having a fraction number of the total energy layers or MU of the initial control point.

2. The method of claim 1, wherein the delivery time of the substantially continuous particle beam is iteratively adjusted via one or more of filtering the one or more energy layers, merging the one or more energy layers, re-distributing the one or more energy layers, or adding new energy layers to the one or more energy layers.

3. The method of claim 1, wherein the delivery time of the substantially continuous particle beam is iteratively adjusted via one or more of filtering one or more proton spots, merging the one or more proton spots, re-distributing the one or more proton spots, or adding new proton spots within and between the one or more proton spots.

4. The method of claim 1, wherein the delivery time of the substantially continuous particle beam is iteratively adjusted via adjusting one or more of the MU of one or more proton spots within and between the control points or an intensity of the one or more proton spots within and between the control points.

5. The method of claim 1, wherein the delivery time of the substantially continuous particle beam is at least partially determined based on a machine-specific delivery sequence model ($DSM_{arc}$) that is calculated using a plurality of machine specific system parameters and a plurality of user defined parameters.

6. The method of claim 5, wherein the plurality of machine specific system parameters includes a delivery tolerance window, gantry mechanical limitations, and mechanism of control point connections.

7. The method of claim 5, wherein the plurality of user defined parameters includes a defined total SPArc delivery time or speed, a delivery tolerance window, and momentum or speed change during delivery of the substantially continuous particle beam.

8. A method of optimizing delivery of a particle beam at a target, wherein the particle beam is delivered from an output device at a plurality of control points, the method comprising:
   delivering a substantially continuous particle beam about the plurality of control points;
   iteratively adjusting a delivery time of the substantially continuous particle beam about the plurality of control points; and
   processing to undertake at least one of (i) pre-defining energy layers based on one or both of the control points and a control point sampling frequency, or (ii) sorting the energy layers.

9. The method of claim 8, wherein the delivery time of the substantially continuous particle beam is iteratively adjusted via one or more of filtering the energy layers, merging the energy layers, re-distributing the energy layers, modifying the energy layers, and adding new energy layers to the energy layers.

10. The method of claim 8, wherein the delivery time of the substantially continuous particle beam is iteratively adjusted via one or more of filtering one or more proton spots, merging the one or more proton spots, re-distributing the one or more proton spots, or adding new proton spots within and between the one or more proton spots.

11. The method of claim 8, wherein the delivery time of the substantially continuous particle beam is iteratively adjusted via adjusting one or more of an MU of one or more proton spots within and between the control points or an intensity of the one or more proton spots within and between the control points.

12. The method of claim 8, wherein the delivery time of the substantially continuous particle beam is at least partially determined based on a machine-specific delivery sequence model ($DSM_{arc}$) that is calculated using a plurality of machine specific system parameters and a plurality of user defined parameters.

13. The method of claim 12, wherein the plurality of machine specific system parameters includes a delivery tolerance window, gantry mechanical limitations, and mechanism of control point connections.

14. The method of claim 12, wherein the plurality of user defined parameters includes a defined total SPArc delivery time or speed, a delivery tolerance window, and momentum or speed change during delivery of the substantially continuous particle beam.

15. A system comprising:

data processing hardware; and memory hardware in communication with the data processing hardware, the memory hardware storing instructions that when executed on the data processing hardware cause the data processing hardware to perform operations comprising:

delivering a substantially continuous particle beam at a target about a plurality of control points;

iteratively adjusting a delivery time of the substantially continuous particle beam about the plurality of control points;

identifying an initial set of control points;

providing a first group of optimized beams, wherein each optimized beam of the first group of optimized beams is configured to be output at a first control point and steered towards one or more energy layers that are associated with one or more monitor unit (MU);

providing a second group of optimized beams, each optimized beam of the second group of optimized beams configured to be output at the first control point and having a reduced number of energy layers;

increasing a number of the initial control points; and maintaining a total number of energy layers as one of equal to, more than, or less than a total number of energy layers associated with the initial control points during movement of the beam between the plurality of control points, wherein increasing the number of initial control points comprises adding one or more adjacent control points to each initial control point, the adjacent control point having a fraction number of the total energy layers or MU of the initial control point.

16. The system of claim 15, wherein the delivery time of the substantially continuous particle beam is iteratively adjusted via one or more of filtering the one or more energy layers, merging the one or more energy layers, re-distributing the one or more energy layers, or adding new energy layers to the one or more energy layers.

17. The system of claim 15, wherein the delivery time of the substantially continuous particle beam is iteratively adjusted via one or more of filtering one or more proton spots, merging the one or more proton spots, re-distributing the one or more proton spots, or adding new proton spots within and between the one or more proton spots.

18. The system of claim 15, wherein the delivery time of the substantially continuous particle beam is iteratively adjusted via adjusting one or more of the MU of one or more proton spots within and between the control points or an intensity of the one or more proton spots within and between the control points.

19. The system of claim 15, wherein the delivery time of the substantially continuous particle beam is at least partially determined based on a machine-specific delivery sequence model ($DSM_{arc}$) that is calculated using a plurality of machine specific system parameters and a plurality of user defined parameters.

20. The system of claim 19, wherein the plurality of machine specific system parameters includes a delivery tolerance window, gantry mechanical limitations, and mechanism of control point connections.

* * * * *